(12) United States Patent
Lebeck et al.

(10) Patent No.: US 11,959,854 B2
(45) Date of Patent: Apr. 16, 2024

(54) RESONATOR NETWORKS FOR IMPROVED LABEL DETECTION, COMPUTATION, ANALYTE SENSING, AND TUNABLE RANDOM NUMBER GENERATION

(71) Applicant: Duke University, Durham, NC (US)

(72) Inventors: Alvin R. Lebeck, Durham, NC (US);
Chris Dwyer, Durham, NC (US);
Craig Laboda, Durham, NC (US)

(73) Assignee: Duke University, Durham, NC (US)

( * ) Notice: Subject to any disclaimer, the term of this patent is extended or adjusted under 35 U.S.C. 154(b) by 216 days.

(21) Appl. No.: 17/363,282

(22) Filed: Jun. 30, 2021

(65) Prior Publication Data

US 2021/0396676 A1    Dec. 23, 2021

Related U.S. Application Data

(62) Division of application No. 16/605,555, filed as application No. PCT/US2018/037076 on Jun. 12, 2018, now Pat. No. 11,674,901.

(Continued)

(51) Int. Cl.
*G01N 21/64*    (2006.01)

(52) U.S. Cl.
CPC ..... *G01N 21/6428* (2013.01); *G01N 21/6408* (2013.01); *G01N 2021/6439* (2013.01)

(58) Field of Classification Search
CPC ........... G01N 21/6428; G01N 21/6408; G01N 2021/6439; G01N 33/582; G01N 21/63; G01N 21/64
See application file for complete search history.

(56) References Cited

U.S. PATENT DOCUMENTS 5,532,129 A    7/1996    Heller
6,207,392 B1   3/2001    Weiss et al.
(Continued)

FOREIGN PATENT DOCUMENTS

CN    102590160 A    7/2012
JP    2007-502992    2/2007
(Continued)

OTHER PUBLICATIONS

LaBoda et al. Acc Chem Res. 2014. 47:1816-1824. (Year: 2014).*
Pistol et al. ASPLOS'09. Mar. 7-11, 2009, Washington, DC, USA. (Year: 2009).*

(Continued)

*Primary Examiner* — Joseph G. Dauner
(74) *Attorney, Agent, or Firm* — POLSINELLI PC

(57) ABSTRACT

The present disclosure provides resonator networks adapted to a variety of applications. The networks include fluorophores, quantum dots, dyes, plasmonic nanorods, or other optical resonators maintained in position relative to each other by a backbone (e.g., a backbone composed of DNA). The networks may exhibit optical absorption and re-emission according to specified temporal decay profiles, e.g., to provide temporally-multiplexed labels for imaging or flow cytometry. The networks can include resonators that exhibit a dark state, such that the behavior of the network can be modified by inducing the dark state in one or more resonators. Such networks could be configured as logic gates or other logical elements, e.g., to provide multiplexed detection of analytes by a single network, to permit the temporal decay profile of the network to be adjusted (e.g., to use the networks as a controllable random number generator), or to provide other benefits.

13 Claims, 12 Drawing Sheets

Related U.S. Application Data

(60) Provisional application No. 62/521,192, filed on Jun. 16, 2017, provisional application No. 62/527,451, filed on Jun. 30, 2017, provisional application No. 62/551,616, filed on Aug. 29, 2017.

(56) References Cited

U.S. PATENT DOCUMENTS

| | | |
|---|---|---|
| 8,067,506 B2 | 11/2011 | Chen et al. |
| 8,309,306 B2 | 11/2012 | Nolan et al. |
| 10,481,161 B2 | 11/2019 | Gaylord et al. |
| 2002/0115092 A1 | 8/2002 | Rebek |
| 2002/0160411 A1 | 10/2002 | Kool |
| 2006/0021673 A1 | 2/2006 | Rodewald |
| 2007/0149732 A1 | 6/2007 | Bazan et al. |
| 2007/0274357 A1 | 11/2007 | Bazan et al. |
| 2007/0275388 A1 | 11/2007 | Ryan |
| 2010/0231920 A1 | 9/2010 | Peled et al. |
| 2010/0291553 A1 | 11/2010 | Nakagawa |
| 2013/0309671 A1 | 11/2013 | Russ et al. |
| 2013/0331530 A1 | 12/2013 | Bazan et al. |
| 2015/0293022 A1 | 10/2015 | Buckhout-White et al. |
| 2016/0130645 A1 | 5/2016 | Huber |
| 2016/0341720 A1 | 11/2016 | Bazan et al. |
| 2017/0074855 A1 | 3/2017 | Morin et al. |
| 2017/0275677 A1 | 9/2017 | Medintz |
| 2017/0309825 A1 | 10/2017 | Bazan et al. |
| 2018/0065998 A1 | 3/2018 | Battrell et al. |
| 2018/0079909 A1 | 3/2018 | Matray et al. |
| 2018/0282474 A1 | 10/2018 | Bazan et al. |
| 2019/0352640 A1 | 11/2019 | Shapiro et al. |

FOREIGN PATENT DOCUMENTS

| | | |
|---|---|---|
| JP | 2012-515905 | 7/2012 |
| JP | 2016-014033 | 1/2016 |
| WO | 2004001379 A2 | 6/2003 |
| WO | 2004077014 A1 | 9/2004 |
| WO | 2004092324 A2 | 10/2004 |
| WO | 2005038944 A1 | 4/2005 |
| WO | 2006029226 A1 | 3/2006 |
| WO | 2006029231 A1 | 3/2006 |
| WO | 2006074471 A2 | 7/2006 |
| WO | 2006094101 A1 | 9/2006 |
| WO | 2007055772 A2 | 5/2007 |
| WO | 2008100344 A1 | 8/2008 |
| WO | 2010151807 A1 | 12/2010 |
| WO | 2011091086 A1 | 7/2011 |
| WO | 2012074853 A1 | 6/2012 |
| WO | 2012174561 A2 | 12/2012 |
| WO | 2012178116 A1 | 12/2012 |
| WO | 2013142850 A1 | 3/2013 |
| WO | 2015/027176 A1 | 2/2015 |
| WO | 2015/109136 A2 | 7/2015 |
| WO | 2017/143171 A1 | 8/2017 |
| WO | 2017/173348 A1 | 10/2017 |
| WO | 2017/173355 A1 | 10/2017 |
| WO | 2017/177065 A2 | 10/2017 |
| WO | 2017/196954 A1 | 11/2017 |
| WO | 2017/197014 A2 | 11/2017 |
| WO | 2017/197144 A1 | 11/2017 |
| WO | 2017/214165 A1 | 12/2017 |
| WO | 2018/022925 A1 | 2/2018 |
| WO | 2018/045278 A1 | 3/2018 |
| WO | 2018044688 A1 | 3/2018 |
| WO | 2019/182765 A1 | 9/2019 |
| WO | 2019/182766 A1 | 9/2019 |
| WO | 2020/006285 A1 | 1/2020 |
| WO | 2020/014634 A1 | 1/2020 |

OTHER PUBLICATIONS

Dutta K. P., et al., "DNA-Directed Artificial Light-Harvesting Antenna," Journal of the American Chemical Society, Jun. 29, 2011, vol. 133(31), pp. 11985-11993.

International Preliminary Report on Patentability for the Application No. PCT/US2018/037076, dated Dec. 26, 2019, 8 pages.

Melinger S.J., et al., "FRET from Multiple Pathways in Fluorophore-Labeled DNA," ACS Photonics, Feb. 24, 2016, vol. 3(4), pp. 659-669.

Pistol C., et al., "Encoded Multichromophore Response for Simultaneous Label-Free Detection," Small, Mar. 26, 2010, vol. 6(7), pp. 843-850.

Search Report and Written Opinion for Singapore Application No. 11201912217W, dated May 15, 2021, 12 pages.

Thusu V., "Self-Assembled Resonance Energy Transfer Devices," PhD Thesis, Duke University, Apr. 30, 2013, 200 Pages.

Olejko, L. et al. (2017) FRET efficiency and antenna effect in multi-color DNA origami-based light harvesting systems. RSC Adv. 7: 23924-23934.

Pan, K. et al. (2014) Structure-based model for light-harvesting properties of nucleic acid nanostructures. Nucleic Acids Research. 42(4): 2159-2170.

Buckhout-White, S. et al. (2012) Multimodal Characterization of a Linear DNA-Based Nanostructure. American Chemical Society. 6(2): 1026-1043.

Hannestad, J. et al. (2011) Self-Assembled DNA-Based Fluorescence Waveguide with Selectable Output. Small. 7 (22): 3178-3185.

Hannestad, J. et al. (2008) Self-Assembled DNA Photonic Wire for Long-Range Energy Transfer. J. Am. Chem. Soc. 130: 15889-15895.

Boeneman, K. et al. (2010) Self-Assembled Quantum Dot-Sensitized Multivalent DNA Photonic Wires. J. Am. Chem. Soc. 132: 18177-18190.

Spillmann, C. et al. (2013) Achieving Effective Terminal Exciton Delivery in Quantum Dot Antenna-Sensitized Multistep DNA Photonic Wires. ACS Nano. 7(8): 7101-7118.

LaBoda et al., "DNA-Enable Integrated Molecular Systems for Computation and Sensing," Acc. Chem. Res. 2014, 47, 1816-1824.

LaBoda et al., "An Optically Modulated Self-Assembled Resonance Energy Transfer Pass Gate," Nano Lett. 2017, 17, 3775-3781.

Wang et al., "fluorescent taggants with temporally coded signatures," Optics Express, vol. 24, No. 14, Jul. 11, 2016, 15528-15545.

Diaz et al., "Extending DNA-Based Molecular Photonic Wires with Homogeneous Forster Resonance Energy Transfer", Advanced Optical Materials, vol. 4, No. 3, Jan. 7, 2016.

Buckhout et al., "Assembling programmable FRET-based photonic networks using designer DNA scaffolds" Nature Communications, vol. 5, No. 1, Dec. 1, 2014.

Dwyer et al., "DNA Self-Assembled Nanostructures for Resonance Energy Transfer Circuits", in: "Nanophotonic Information Physics", Jan. 1, 2014.

Rowland et al., "Growing applications for bioassembled Forster resonance energy transfer cascades", Materials Today, vol. 20, No. 3, Apr. 2014.

Extended European Search Report dated Jun. 1, 2021 for corresponding European Patent Application 18818190.3, 13 pages.

International Search Report of International Application No. PCT/US2018/037076, dated Jan. 11, 2019, 4 pages.

Zhang, K. et al. (2012) Antibody-Linked Spherical Nucleic Acids for Cellular Targeting. Journal of the American Chemical Society. 134 (40): 16488-16491.

Tong, A. et al. (2001) Combinatorial fluorescence energy transfer tags for multiplex biological assays. Nature Biotechnology. 19: 756-759.

Zhu, L. et al. (2003) Fluorescence Multiplexing with Time-Resolved and Spectral Discrimination Using a Near-IR Detector. Analytical Chemistry. 75(10): 2280-2291.

\* cited by examiner

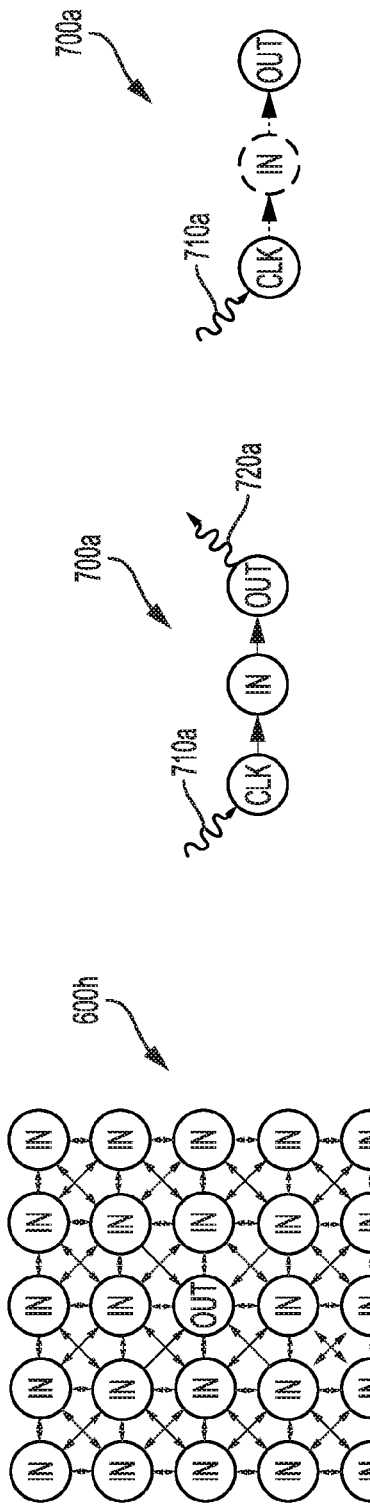
FIG. 7B
FIG. 7D
FIG. 7A
FIG. 7C
FIG. 6H

RESONATOR NETWORKS FOR IMPROVED LABEL DETECTION, COMPUTATION, ANALYTE SENSING, AND TUNABLE RANDOM NUMBER GENERATION

CROSS-REFERENCE TO RELATED APPLICATIONS

This application is a division of U.S. patent application Ser. No. 16/605,555, now U.S. Pat. No. 11,674,901, filed Oct. 16, 2019, which is a U.S. national phase application of International Patent Application No. PCT/US2018/037076, filed Jun. 12, 2018, which claims priority to U.S. Provisional Patent Application No. 62/521,192, filed Jun. 16, 2017, U.S. Provisional Patent Application No. 62/527,451, filed Jun. 30, 2017, and U.S. Provisional Patent Application No. 62/551,616, filed Aug. 29, 2017 which are incorporated herein by reference.

BACKGROUND

A variety of fluorophores, quantum dots, Raman dyes, and other optically active substances can be incorporated into labels. Such labels can be used to determine the presence, location, amount, or other properties of the label and/or of an analyte to which the label is configured to bind in a sample. This can include illuminating the sample at one or more optical wavelengths and detecting light responsively reflected by, absorbed and fluorescently re-emitted by, or otherwise emitted from the label. A timing, a spectral content, an intensity, a degree of polarization, or some other property of light detected from the sample in response to illumination of the sample could be used to detect the identity of the label in the sample. For example, a library of labels, differing with respect to an excitation spectrum, an emission spectrum, a susceptibility to photobleaching, or some other optical property, could be applied to the sample in order to detect the presence, location, or other properties of a respective plurality of analytes in the sample.

In some examples, a label can include multiple fluorophores in sufficient proximity that energy can pass from an absorbing donor fluorophore of the label to an emitting acceptor fluorophore of the label. In such examples, a state of binding to a target analyte or some other status of such a label could be related to a distance between the donor and acceptor. That is, the label binding to an instance of an analyte could cause a conformation change in the label such that the distance between the donor and acceptor increases (or decreases) to such a degree that energy is less (or more) likely to transfer from the donor to the acceptor. In such examples, a degree of overall fluorescence of the label, or some other optical property of the label, could be detected and used to determine the presence, location, amount, an isoform, or some other property of the analyte in a sample.

SUMMARY

One aspect of the present disclosure provides a label including: (i) two or more input resonators that each include at least one of a fluorophore, a quantum dot, or a dye; (ii) an output resonator that includes at least one of a fluorophore or a quantum dot; and (iii) an organic backbone. The two or more input resonators and the output resonator are coupled to the backbone and the backbone maintains relative locations of the input resonators and the output resonator such that energy can be transmitted from each of the input resonators to the output resonator.

Another aspect of the present disclosure provides a label including: (i) an input resonator; (ii) one or more mediating resonators, where a first one of the one or more mediating resonators is disposed proximate to the input resonator such that the first mediating resonator can receive energy from the input resonator; (iii) an output resonator, where at least one of the one or more mediating resonators is disposed within the label proximate to the output resonator such that the output resonator can receive energy from the at least one of the one or more mediating resonators; and (iv) a backbone. The input resonator, the output resonator, and the one or more mediating resonators are coupled to the backbone and the backbone maintains relative locations of the input resonator, the output resonator, and the one or more mediating resonators such that energy can be transmitted from the input resonator to the output resonator via the one or more mediating resonators.

Another aspect of the present disclosure provides a system including: (i) a sample container; (ii) a light source; (iii) a light detector; and (iv) a controller. The controller is programmed to perform operations including: (a) illuminating, using the light source, the sample container; (b) using the light detector, detecting a timing, relative to the illumination of the sample container, of emission of a plurality of photons from the sample container within a range of detection wavelengths; and (c) determining, based on the detected timing of emission of the plurality of photons, an identity of a label. Determining the identity of the label includes selecting the identity of the label from a set of known labels. The label includes: (1) an input resonator; (2) an output resonator, where the output resonator is characterized by an emission wavelength and the range of detection wavelengths includes the emission wavelength of the output resonator; and (3) a network of one or more mediating resonators, where relative locations of the input resonator, the output resonator, and the one or more mediating resonators within the label are such that energy can be transmitted from the input resonator to the output resonator via the one or more mediating resonators in response to the input resonator being excited by the illumination.

Yet another aspect of the present disclosure provides anon-transitory computer-readable medium having stored thereon instructions executable by at least one processor to perform functions including: (i) illuminating a sample that contains a label; (ii) detecting a timing, relative to the illumination of the sample, of emission of a plurality of photons from the sample within a range of detection wavelengths, where the range of detection wavelengths includes an emission wavelength of an output resonator of the label; and (iii) determining, based on the detected timing of emission of the plurality of photons, an identity of the label. The label includes: (a) an input resonator; (b) an output resonator, where the output resonator is characterized by an emission wavelength; and (c) a network of one or more mediating resonators, where relative locations of the input resonator, the output resonator, and the one or more mediating resonators within the label are such that energy can be transmitted from the input resonator to the output resonator via the network of one or more mediating resonators in response to the input resonator being excited by the illumination. Determining the identity of the label includes selecting the identity of the label from a set of known labels.

Yet another aspect of the present disclosure provides a contrast agent including: (i) a first label; and (ii) a second label. The first label includes: (a) a first receptor that selectively interacts with a first analyte of interest; (b) at least two first input resonators; (c) at least one first output resonator, where a ratio between a number of first input resonators in the first label and a number of first output resonators in the first label has a first value; and (d) a first backbone, where the first receptor, the at least two first input resonators, and the at least one first output resonator are coupled to the first backbone, and the first backbone maintains relative locations of the at least two first input resonators and the at least one first output resonator such that energy can be transmitted from each of the first input resonators to at least one first output resonator. The second label includes: (a) a second receptor that selectively interacts with a second analyte of interest; (b) at least two second input resonators; (c) at least one second output resonator, where a ratio between a number of second input resonators in the second label and a number of second output resonators in the second label has a second value; and (d) a second backbone, where the second receptor, the at least two second input resonators, and the at least one second output resonator are coupled to the second backbone, and the second backbone maintains relative locations of the at least two second input resonators and the at least one second output resonator such that energy can be transmitted from each of the second input resonators to at least one second output resonator. Further, the first value and the second value differ Yet another aspect of the present disclosure provides a method including: (i) illuminating a sample that contains a label; (ii) detecting a timing, relative to the illumination of the sample, of emission of a plurality of photons from the sample within a range of detection wavelengths, wherein the range of detection wavelengths includes an emission wavelength of an output resonator of the label; and (iii) determining, based on the detected timing of emission of the plurality of photons, an identity of the label. The label includes: (a) an input resonator; (b) an output resonator that is characterized by an emission wavelength; and (c) a network of one or more mediating resonators, where relative locations of the input resonator, the output resonator, and the one or more mediating resonators within the label are such that energy can be transmitted from the input resonator to the output resonator via the network of one or more mediating resonators in response to the input resonator being excited by the illumination. Determining the identity of the label includes selecting the identity of the label from a set of known labels.

Yet another aspect of the present disclosure provides a system including: (i) a sample container; (ii) a light source; (iii) a light detector; and (iv) a controller. The controller is programmed to perform operations including: (a) illuminating, using the light source, the sample container; (b) using the light detector, detecting a timing, relative to the illumination of the sample container, of emission of a plurality of photons from the sample container within a range of detection wavelengths; and (c) determining, based on the detected timing of emission of the plurality of photons, an identity of a label. Determining the identity of the label includes selecting the identity of the label from a set of known labels. The label includes: an input resonator that is characterized by an emission wavelength, where the range of detection wavelengths includes the emission wavelength of the input resonator; and (b) a modulating resonator, where relative locations of the input resonator and the modulating resonator within the label are such that energy can be transmitted between the input resonator and the modulating resonator in response to the input resonator being excited by the illumination.

Yet another aspect of the present disclosure provides a resonator network including: (i) a first input resonator that has a dark state, where the first input resonator can enter the dark state in response to receiving illumination at a first input excitation wavelength; (ii) a readout resonator that can receive energy from illumination at a readout wavelength; (iii) an output resonator; and (iv) a backbone. The first input resonator, the readout resonator, and the output resonator are coupled to the backbone, and the backbone maintains relative locations of the first input resonator, the readout resonator, and the output resonator such that energy can be transmitted from the readout resonator to the output resonator and further such that a probability of energy being transmitted from the readout resonator to the output resonator is related to whether the first input resonator is in the dark state.

Yet another aspect of the present disclosure provides a method for detecting an analyte, the method including: (i) illuminating a resonator network, during a first period of time, with light at a first input wavelength; (ii) illuminating the resonator network, during the first period of time, with light at a readout wavelength; and (iii) detecting, during the first period of time, an intensity of light emitted from an output resonator of the resonator network. The resonator network includes: (a) a first input resonator that has a dark state, where the first input resonator can enter the dark state in response to receiving illumination at the first input excitation wavelength; (b) a readout resonator that can receive energy from illumination at the readout wavelength; (c) a mediating resonator; (d) an output resonator; (e) a sensor that includes a receptor that preferentially binds to an analyte; and (f) a backbone. The first input resonator, the readout resonator, the sensor, and the output resonator are coupled to the backbone, and the backbone maintains relative locations of the first input resonator, the readout resonator, the mediating resonator, the sensor, and the output resonator such that energy can be transmitted from the readout resonator to the output resonator via the mediating resonator and further such that a probability of energy being transmitted from the readout resonator to the output resonator, when the first input resonator is in the dark state, is related to whether the receptor is bound to an instance of the analyte.

Yet another aspect of the present disclosure provides a method including: (i) illuminating a plurality of resonator networks, during a first period of time, with light at a first input wavelength; (ii) illuminating the plurality of resonator networks, during the first period of time, with light at a readout wavelength; and (iii) detecting a timing, relative to the illumination of the resonator networks, of emission of a plurality of photons from output resonators of the plurality of resonator networks. Each resonator network of the plurality of resonator networks includes: (a) a first input resonator that has a dark state and that can enter the dark state in response to receiving illumination at the first input excitation wavelength; (b) a readout resonator that can receive energy from illumination at the readout wavelength; (c) two or more mediating resonators; (d) an output resonator; and (e) a backbone. The first input resonator, the readout resonator, the two or more mediating resonators, and the output resonator are coupled to the backbone, and the backbone maintains relative locations of the first input resonator, the readout resonator, the two or more mediating resonators, and the output resonator such that energy can be transmitted from the readout resonator to the output resonator via the mediating resonator and further such that the resonator network emits photons from the output resonator, in response to the readout resonator receiving illumination at the readout wavelength, according to a time-dependent probability density function. A detectable property of the time-dependent probability density function is related to whether the first input resonator is in the dark state.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6H shows a schematic of resonators in a label.
FIG. 7A shows a schematic of resonators in a network.
FIG. 7B shows a schematic of resonators in a network.
FIG. 7C shows a schematic of resonators in a network.
FIG. 7D shows a schematic of resonators in a network.

DETAILED DESCRIPTION

Figure 1A:
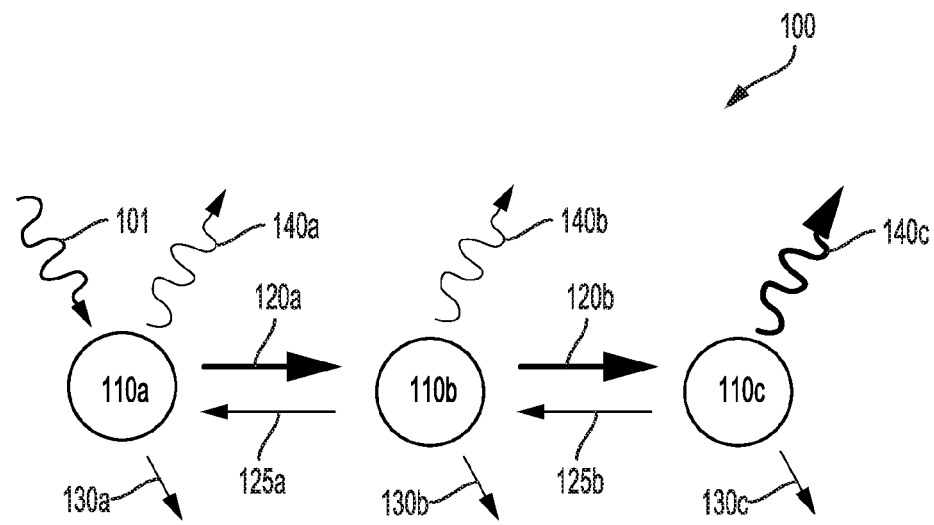
FIG. 1A shows a schematic of resonators in a label.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

DNA self-assembly and other emerging nano-scale manufacturing techniques permit the fabrication of many instances of a specified structure with precision at the nano-scale. Such precision may permit fluorophores, quantum dots, dye molecules, plasmonic nanorods, or other optical resonators to be positioned at precise locations and/or orientations relative to each other in order to create a variety of optical resonator networks. Such resonator networks may be specified to facilitate a variety of different applications. In some examples, the resonator networks could be designed such that they exhibit a pre-specified temporal relationship between optical excitation (e.g., by a pulse of illumination) and re-emission; this could enable temporally-multiplexed labels and taggants that could be detected using a single excitation wavelength and a single detection wavelength. Additionally or alternatively, the probabilistic nature of the timing of optical re-emission, relative to excitation, by these resonator networks could be leveraged to generate samples of a random variable. These resonator networks may include one or more "input resonators" that exhibit a dark state; resonator networks including such input resonators may be configured to implement logic gates or other structures to control the flow of excitons or other energy through the resonator network. Such structures could then be used, e.g., to permit the detection of a variety of different analytes by a single resonator network, to control a distribution of a random variable generated using the resonator network, to further multiplex a set of labels used to image a biological sample, or to facilitate some other application.

These resonator networks include networks of fluorophores, quantum dots, dyes, Raman dyes, conductive nanorods, chromophores, or other optical resonator structures. The networks can additionally include antibodies, aptamers, strands of deoxyribonucleic acid (DNA) or ribonucleic acid (RNA), or other receptors configured to permit selective binding to analytes of interest (e.g., to a surface protein, molecular epitope, characteristic nucleotide sequence, or other characteristic feature of an analyte of interest). The labels could be used to observe a sample, to identify contents of the sample (e.g., to identity cells, proteins, or other particles or substances within the sample), to sort such contents based on their identification (e.g., to sort cells within a flow cytometer according to identified cell type or other properties), or to facilitate some other applications.

In an example application, such resonator networks may be applied (e.g., by coupling the resonator network to an antibody, aptamer, or other analyte-specific receptor) to detect the presence of, discriminate between, or otherwise observe a large number of different labels in a biological or material sample or other environment of interest. Such labels may permit detection of the presence, amount, or location of one or more analytes of interest in a sample (e.g., in a channel of a flow cytometry apparatus). Having access to a large library of distinguishable labels can allow for the simultaneous detection of a large number of different analytes. Additionally or alternatively, access to a large library of distinguishable labels can allow for more accurate detection of a particular analyte (e.g., a cell type or sub-type of interest) by using multiple labels to bind with the same analyte, e.g., to different epitopes, surface proteins, or other features of the analyte. Yet further, access to such a large library of labels may permit selection of labels according to the probable density or number of corresponding analytes of interest, e.g., to ensure that the effective brightness of different labels, corresponding to analytes having different concentrations in a sample, is approximately the same when optically interrogating such a sample.

Such labels may be distinguishable by virtue of differing with respect to an excitation spectrum, an emission spectrum, a fluorescence lifetime, a fluorescence intensity, a susceptibility to photobleaching, a fluorescence dependence on binding to an analyte or on some other environmental factor, a polarization of re-emitted light, or some other optical properties. However, it can be difficult to produce a large library of distinguishable labels when relying on differences with respect to emission or excitation spectrum due to limitations on the available fluorophores or other optical distinguishable substances and limitations on the wavelength transparency/compatibility of common sample materials of interest.

The present disclosure provides methods for specifying, fabricating, detecting, and identifying optical labels that differ with respect to temporal decay profile and/or excitation and emission spectra. Additionally or alternatively, the provided labels may have enhanced brightness relative to existing labels (e.g., fluorophore-based labels) and may have a configurable brightness to facilitate panel design or to permit the relative brightness of different labels to facilitate some other consideration. Such labels can differ with respect to the time-dependent probability of re-emission of light by the label subsequent to excitation of the label (e.g., by an ultra-fast laser pulse). Additionally or alternatively, such labels can include networks of resonators to increase a difference between the excitation wavelength of the labels and the emission wavelength of the labels (e.g., by interposing a number of mediating resonators between an input resonator and an output resonator to permit excitons to be transmitted between input resonators and output resonators between which direct energy transfer is disfavored). Yet further, such labels may include logic gates or other optically-controllable structures to permit further multiplexing when detecting and identifying the labels.

Since such labels may differ with respect to temporal decay profile, they may be detected and identified in a sample by illuminating the sample with a single wavelength of illumination and/or by detecting responsively emitted light from the sample within a narrow band of wavelengths. Such a detection paradigm could simplify apparatuses used to interrogate samples containing such labels and/or could facilitate high-label-count interrogation of sample media having strict optical requirements (e.g., that exhibit significant auto-fluorescence, that are particular sensitive to photobleaching or other deleterious optical effects, that have narrow bands of transparency).

Each label (or other resonator network as described herein) includes at least one input resonator that is capable of receiving optical energy to excite the network (e.g., energy from an interrogating laser pulse) and at least one output resonator that is capable of emitting a photon in response to receiving, via the resonator network, energy (e.g., as an exciton transmitted via Forster resonance energy transfer (FRET) and/or some other mechanism) from the input resonator. The relative locations of the input resonator(s), output resonator(s), and one or more additional mediator resonators permit the transfer of excitons, electrical fields, surface plasmons, or other energy from resonator to resonator such that, when a particular resonator of the network is excited (e.g., the input resonator), it has a chance to transfer that excitation energy to one or more other resonators (e.g., the output resonator). The number and arrangement of resonators present in each instance of such a label (e.g., a number of input resonators of each instance of a label) may be specified to set a brightness of the label (e.g., to normalize the intensity of light emitted from a sample by different labels that may have bound to analytes present in the sample).

The temporal decay profile of a particular label may thus be related to the properties of the resonator network, e.g., to the identity and properties (e.g., probability of nonradiative decay, probability of resonance energy transfer to another resonator, or probability of radiative emission) of the resonators and the relative locations and orientations of the resonators within the network. For example, a number of mediating resonators could be arranged sequentially between an input resonator and an output resonator to form a resonator wire. The temporal decay profile of such a resonator network could be related to the length of the wire, e.g., longer wires could exhibit decay profiles that have wider peaks situated later in time. A library of distinguishable labels could be created by varying the properties of the resonance network for each of the labels such that the corresponding decay profiles of the labels are distinguishable. Thus, the presence, identity, or other properties of such labels in a sample could be detected by illuminating the sample and detecting a timing, relative to the illumination, of emission of photons from the sample.

Additionally or alternatively, the probabilistic nature of the time difference between excitation and re-emission of light from such resonator networks may be leveraged to generate samples of a random variable. The temporal decay profile of such a resonator network could be static (that is, set by the structure of the network and not easily modified or controlled); in such examples, the timing of photon re-emission from such a network (or from a population of such networks) could be used to generate samples of a single random variable that is related to the static temporal decay profile of the network. Alternatively, such a network could include one or more input resonators that exhibit a dark state (i.e., that may be disabled, with respect to their ability to transmit and/or receive energy to/from other resonators in the network) when appropriately optically stimulated. Such input resonators may be used to adjust the temporal decay profile of the network over time, e.g., to permit use of the resonator network to generate samples of a variety of different random variables that are related to respective different, optically-controllable temporal decay profiles of the network.

Such dark state-exhibiting resonators may be incorporated into the network such that their being in a dark state inhibits and/or facilitates transmission of energy between different portions (e.g., between an input and an output) of the network. For example, such an input resonator could be situated between two other resonators such that, when the input resonator was in a dark state, energy transmission between the two other resonators, via the input resonator, is impeded. In another example, an input resonator could be placed within a network such that, when the input resonator was not in a dark state, the input resonator preferentially received energy from one or more other resonators in the network. Thus, placing the input resonator into the dark state could act to prevent the input resonator from "sinking" energy from the network.

Such dark state-exhibiting resonators may thus be incorporated into a resonator network in order to provide logical functions within the network. For example, such a resonator network may be configured to execute a logical computation, with inputs being "programmed" into the network by inducing relevant input resonators to enter their dark states (e.g., by illuminating them with illumination at an excitation wavelength of the input resonator(s)). The logical computation could then be "read out" by optically exciting an additional resonator of the network (a "readout resonator") and detecting photons responsively emitted from an output resonator of the network.

Such resonator networks may also be used for sensing properties of a sample or another environment of interest, e.g., to detect a presence or amount of one or more analytes of interest in a biological sample. One or more resonators of the network could be intrinsically sensitive to a variable of interest (e.g., a resonator could be quenched when environmental pH is within a particular range). Additionally or alternatively, the network may include a sensor configured to alter one or more detectable properties (e.g., a probability of re-emission in response to excitation, a temporal decay profile of excitation and re-emission) of the resonator network. For example, the network may include a receptor (e.g., an antibody, an aptamer, a strand of complementary DNA or RNA) that quenches a resonator of the network when bound to an analyte, that quenches a resonator of the network when not bound to the analyte, that modifies a relative location of one or more resonators of the network when bound to the analyte, or that otherwise modifies the configuration and/or behavior of the resonator network depending on whether it is bound to an instance of the analyte. Such a resonator network may include logical elements (e.g., one or more dark-state-exhibiting resonators) such that a number of different analytes may be detected using a single resonator network (e.g., by controlling the dark-state input resonators to "address" a particular one of a variety of different receptors of the network).

The resonator network of such a label could be created via a variety of techniques. In some examples, DNA self-assembly could be used to ensure that the relative locations of the resonators within a label correspond to locations specified according to a desired temporal decay profile. For example, each resonator of the network could be coupled to a respective specified DNA strand. Each DNA strand could include one or more portions that complement portions one or more other DNA strands such that the DNA strands self-assemble into a nanostructure that maintains the resonators at the specified relative locations.

II. Labels Using Specified Resonator Networks for Temporal Multiplexing

Labels as described herein can be created that distinguishably differ with respect to their temporal decay profiles in response to illumination. This can be accomplished by specifying the identity, number, relative location and/or orientation, topology, or other properties of a network of resonators of the label. These properties of the resonator can be specified such that the resulting temporal decay profile corresponds to a desired temporal decay profile. For example, the resonator network of a label could be specified such that the temporal decay profile of the label includes one or more peaks having respective specified widths, normalized amplitudes, mean delay times, or other properties or features such that the temporal decay profile of the label is distinguishable from one or more other labels and/or from background materials present in a sample or environment of interest (e.g., fluorescent proteins of a cell or other biological sample).

Generally, the resonator network of such labels includes at least one input resonator, one or more mediating resonators, and at least one output resonator. The resonators may be fluorophores, Raman dyes, quantum dots, dyes, pigments, conductive nanorods or other nanostructures, chromophores, or other substances that can receive energy from and/or transmit energy to one or more other resonators in the network in the form of an exciton, an electrical fields, a surface plasmon, or some other form of energy that may be transferred, in a unitary manner, from one resonator to another.

The at least one input resonator of the network can receive energy into the network as a result of the label being illuminated (e.g., by a laser pulse having a wavelength corresponding to an excitation wavelength of the input resonator). The at least one output resonator of the network can transmit energy from the network in the form of a photon whose timing of emission, relative to illumination of the label, may be detected and used, along with a plurality of additional photons detected from a sample (e.g., from additional instances of the label in the sample, or from the particular instance of the label as a result of repeated illumination of the sample), to identify the label. The input resonator, output resonator, and one or more mediating resonators are arranged to form the resonator network such that energy (e.g., excitons) received into the network via the input resonator(s) can be transmitted through the network to the output resonator(s).

Note that the labeling of any particular resonator in a network as "input," "mediating," or "output" is meant to be non-limiting. A particular resonator of a network could act as a mediating resonator for one or more other resonators and could also act as an input resonator and/or as an output resonator for the network. Further, a label as described herein could include only two resonators (e.g., an "input" resonator and a "modulating" resonator) and could be interrogated as described herein by exposing the label to illumination that can excite at least the input resonator and by detecting the timing, relative to the illumination, of emission of a plurality of photons responsively emitted from at least one of the input resonator or the modulating resonator. The input resonator (e.g., a fluorophore, a conductive nanorod or other nanoparticles, a quantum dot) could be disposed within the label such that energy (e.g., excitons, electrical fields) can transfer from the input resonator to the modulating resonator (e.g., a fluorophore, a conductive nanorod or other nanoparticles, a quantum dot, a non-fluorescent optically absorptive molecule or substance) and/or from the modulating resonator back to the input resonator.

The identity of such a two-resonator label, or of some other label as described herein that can emit light from the same resonator by which the label can receive energy from illumination, could then be determined based on the detected relative timing of the emission of the plurality of photons. For example, the label could be identified by comparing the detected timing to a set of known temporal decay profiles, wherein the label corresponds to one of the temporal decay profiles in the set of known temporal decay profiles. In such an example, the temporal decay profile of the label could be adjusted by specifying the identity of the resonators and by precisely controlling the relative locations and/or orientations of the resonators (e.g., using DNA self-assembly).

The particular configuration of the resonators and of the resonator network as a whole result in the timing of emission of photons from the output resonator (or from the input resonator, a mediating resonator, a modulating resonator, or some other resonator of the label), relative to illumination of the label, exhibiting a characteristic temporal delay profile. Thus, the timing of emission of a plurality of photons from a sample relative to illumination of the sample (during one or more illumination periods) could be detected and used to identify the label in the sample, or to identify one or more additional labels in the sample, based on the characteristic temporal decay profile(s) of the label(s) in the sample.

FIG. 1A illustrates a schematic of resonators, and potential energy transfers to and from those resonators, of an example label 100 as described herein. The example label 100 includes an input resonator 110a, a mediating resonator 110b, and an output resonator 110c. The input resonator 110a can be excited by receiving illumination 101 from the environment of the label 100. Once excited, the input resonator 110a can radiatively emit a photon 140a, nonradiatively decay 130a such that the energy is lost (e.g., as heat) to the environment, or transfer energy 120a to the mediating resonator 110b (e.g., via the Förster resonance energy transfer process). In response to being excited, the mediating resonator 110b can radiatively emit a photon 140b, nonradiatively decay 130b, transfer energy 120b to the output resonator 110c, or transfer energy 125a to the input resonator 110a. The output resonator 110c, in response to being excited, can radiatively emit a photon 140c, nonradiatively decay 130c, or transfer energy 125b to the mediating resonator 110b.

By way of example, the relative probability of the different energy transitions/transfers are indicated in FIG. 1A by the relative line weight of their representative arrows. Thus, for the example label 100, it is most likely that the input resonator 110a transfers energy to the mediating resonator 110b, that the mediating resonator 110b transfers energy to the output resonator 110c, and that the output resonator 110c radiatively emits a photon 140c.

The time-dependence of each transition from a particular resonator can be represented by a random variable having a particular distribution over time. For example, the mediating resonator 110b transferring energy (e.g., transferring an exciton) to the output resonator 110c could occur according to an exponentially distributed random variable in the time domain. These random variables, along with the structure and other properties of the resonator network of the label 100, can be used to model the behavior of the label 100, e.g., using a continuous time Markov chain. Such a model can then be used to predict the overall temporal decay profile of the label 100 from excitation of the input resonator 110a by the illumination 101 to emission of a photon 140c by the output resonator 110c.

Figure 1B:
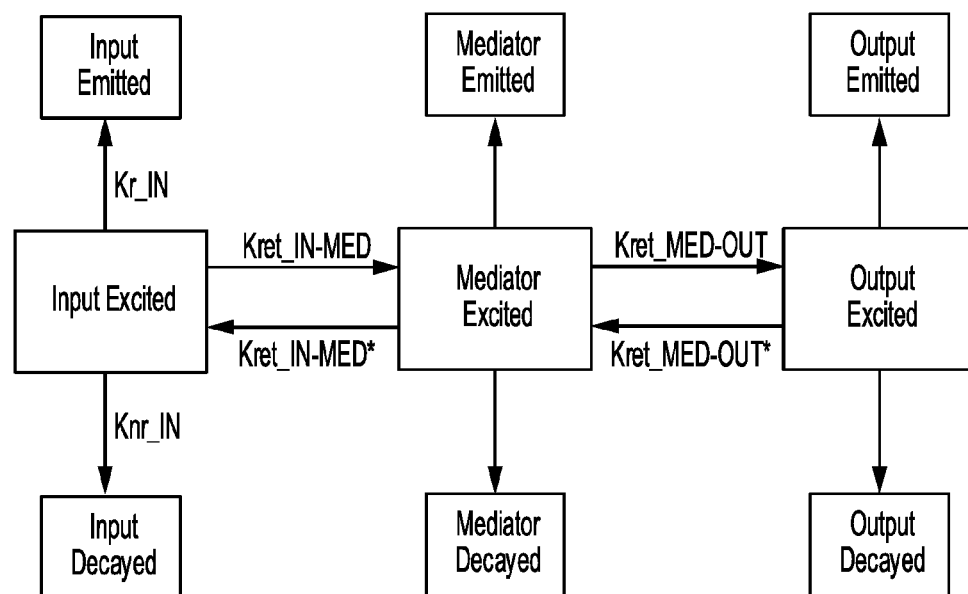
FIG. 1B shows a state transition diagram of the label illustrated schematically in FIG. 1A.

FIG. 1B illustrates a state diagram that could be used to model the potential states of the label 100, according to the excitation states of the resonators. This model assumes that only one of the resonators of the label 100 can be excited, as only a single unit of energy (e.g., a single exciton) is received from the illumination 101 via the input resonator 110a. This unit of energy can then be transferred between the resonators and/or can exit the resonator network (e.g., via emission of a photon or by non-radiative decay processes). The model includes states for excitation of the input resonator 110a ("Input Excited"), the mediating resonator 110b ("Mediator Excited"), and the output resonator 110c ("Output Excited"). The model also includes absorbing states for non-radiative decay from each of the resonators ("Input Decayed," "Mediator Decayed," and "Output Decayed") and radiative photon emission from each of the resonators ("Input Emitted," "Mediator Emitted," and "Output Emitted").

The transition probabilities for each transition are also indicated. These transition probabilities can be related to the identity of the resonators (e.g., to their intrinsic fluorescence lifetime, Förster radius), to their relative location, distance, and/or orientation (e.g., distance relative to the Förster radius of a pair of the resonators), or to some other properties of the label 100. Thus, the relative locations and identities of the resonators within the resonator network can be specified to control the transition probabilities and topology of the model, and thus to control the predicted temporal decay profile of the label 100.

Figure 2A:
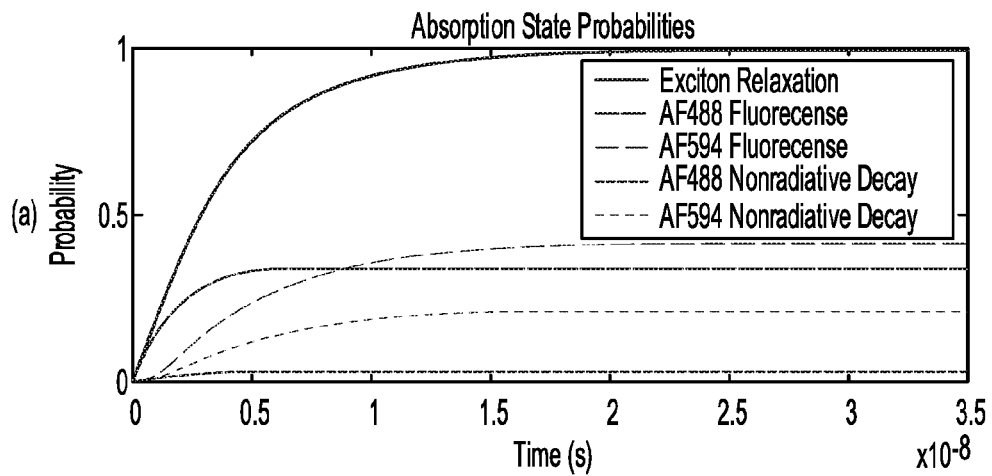
FIG. 2A shows the cumulative probability, over time, that a variety of terminal states of a label have occurred.

In an example, a label includes an ALEXA FLUOR® 448 dye as an input resonator and an ALEXA FLUOR® 594 dye as an output resonator, with the input resonator and output resonator located proximate to each other such that the input resonator can transmit energy, as an exciton, to the output resonator in response to the input resonator being excited by illumination (e.g., an ultrashort laser pulse). FIG. 2A illustrates the probability, over time, that the input resonator ("AF448 Fluorescence") has emitted a photon, that the input resonator has decayed ("AF448 Nonradiative Decay"), that the output resonator ("AF594 Fluorescence") has emitted a photon, and that the output resonator has decayed ("AF594 Nonradiative Decay"). FIG. 2A also illustrates the probability, over time, that at least one of these processes has occurred ("Exciton relaxation").

Figure 2B:
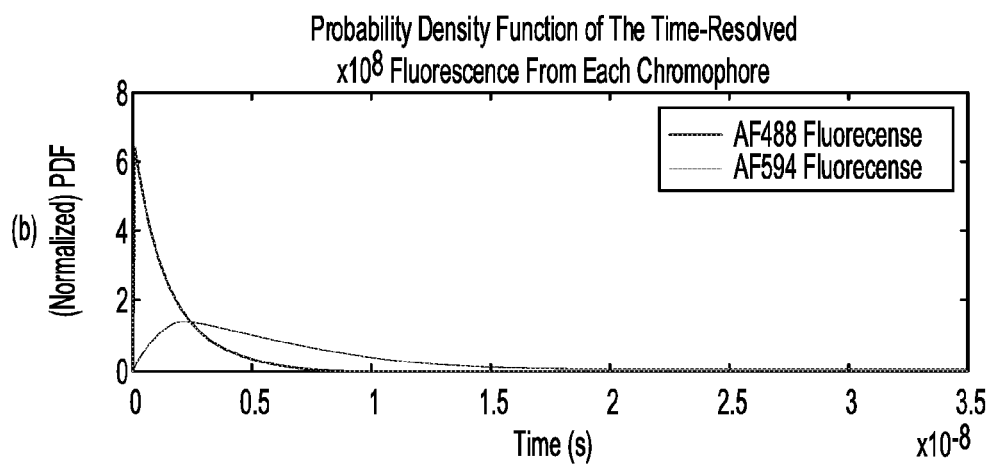
FIG. 2B shows the probability that a label will emit a photon as a function of time following excitation of the label.

From these probabilities, we can determine the temporal decay profile of the label. This is illustrated in FIG. 2B as "AF594 Fluorescence." Thus, if a plurality of instances of the label was present in the sample and/or if a sample containing a single instance of the label was illuminated a plurality of times, the timing of emission of photons from the output resonator (e.g., at an emission wavelength of the ALEXA FLUOR® 594 dye) would exhibit a distribution over time, relative to illumination of the sample, corresponding to the illustrated temporal decay profile. Conversely, the timing of emission of photons from the input resonator (e.g., at an emission wavelength of the ALEXA FLUOR® 488 dye) would exhibit a distribution over time, relative to illumination of the sample, corresponding to the other temporal decay profile illustrated in FIG. 2B ("AF488 Fluorescence").

The temporal decay profile of a particular label at a particular wavelength (e.g., the emission wavelength of an output resonator of the label) could be controlled by specifying the topology, structure, resonators types, or other properties of the resonator network of the label. Thus, a library of different, distinguishable labels could be created by specifying their respective resonator networks such that their temporal decay profiles are distinguishable (e.g., by a particular detection apparatus having a particular temporal resolution for detection of photons from a sample containing such labels) from each other and/or from background processes (e.g., fluorescence) in a sample or other environment of interest. This could include specifying the temporal decay profiles to maximize or increase a measure of statistical divergence (e.g., a Kullback-Leibler divergence, a Jensen-Shannon divergence, a Bregman divergence, or a Fisher information metric) between the temporal decay profiles. Additionally or alternatively, the temporal decay profiles could be specified to differ with respect to the timing, width, shape, number, or other properties of one or more peaks present in the temporal decay profiles.

A resonator network could be determined to provide a desired temporal decay profile using a variety of methods. For example, heuristic methods could be used to vary a number of resonators in a resonator wire of the network, a number a parallel resonator wires in a network between an input and an output of the network, an identity of resonators (e.g., relative to excitation and/or emission spectra of the resonators) of the network, or other properties of the network in order to provide related changes in a number, width, or delay of peaks in a temporal decay profile, an average delay of the temporal decay profile, or other properties of the temporal decay profile. Additionally or alternatively, automated methods like genetic algorithms, machine learning, or other techniques could be used to specify the configuration of one or more resonator network such that their temporal decay profiles are distinguishable or to provide some other benefit. The temporal decay profile of such labels could then be verified experimentally, and the experimentally determined temporal decay profiles could be used to identify the labels present in a sample or other environment of interest.

Figures 3A, 3B, 3C, 3D, 3E, 3F:
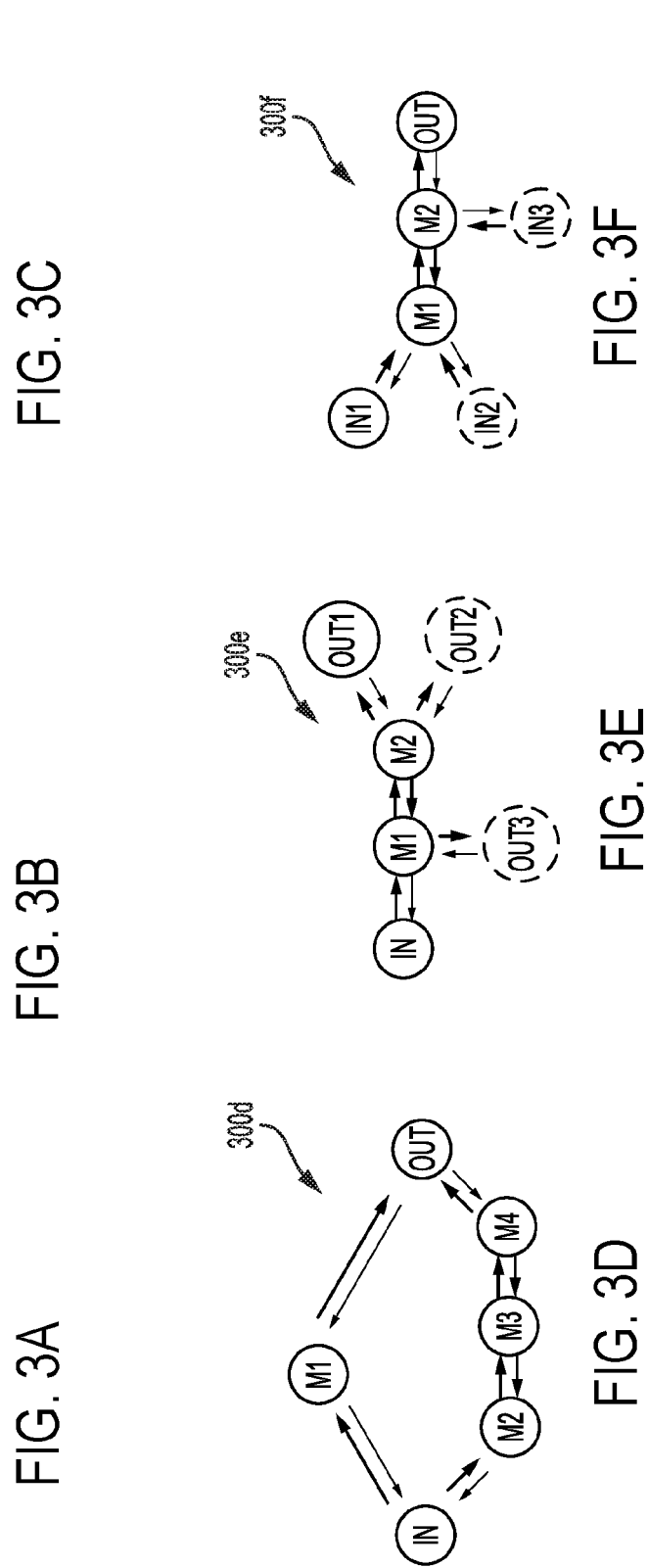
FIG. 3A shows a schematic of resonators in a label.
FIG. 3B shows a schematic of resonators in a label.
FIG. 3C shows a schematic of resonators in a label.
FIG. 3D shows a schematic of resonators in a label.
FIG. 3E shows a schematic of resonators in a label.
FIG. 3F shows a schematic of resonators in a label.

FIG. 3A illustrates a schematic of resonators, and potential energy transfers to and from those resonators, of an example label 300a as described herein. The example label 300a includes an input resonator ("IN"), two mediating resonators ("M1" and "M2"), and an output resonator ("OUT"). The input resonator can be excited by receiving illumination from the environment of the label 300a (e.g., illumination at an excitation wavelength of the input resonator). The two mediating resonators are arranged as a resonator wire between the input resonator and the output resonator. That is, the two mediating resonators are arranged such that each resonator in the wire can receive energy from and/or transmit energy to two neighboring resonators. The number of resonators within such a resonator wire could be specified in order to adjust a temporal decay profile of the label 300a, e.g., to adjust a delay or width of a peak in the decay profile, to increase an average decay of the decay profile, or to adjust some other property of the temporal decay profile.

By way of example, the relative probability of the different energy transfers between the resonators are indicated in FIG. 3A by the relative line weight of their representative arrows. Thus, for the example label 300a, it is more likely that the input resonator transfers energy to the first mediating resonator (M1) than vice versa. It is also more likely that the second mediating resonator (M2) transfers energy to output resonator than vice versa. It is approximately equally likely that the first mediating resonator transfers energy to the second mediating resonator as it is that the second mediating resonator transfers energy to the first mediating resonator. Thus, energy generally travels unidirectionally from the input resonator to the mediating resonators and from the mediating resonators to the output resonators. Conversely, energy may travel bidirectionally between the mediating resonators before being emitted as a photon from the output resonator (or from one of the mediating resonators) or lost via non-radiative processes.

The label 300a of FIG. 3A illustrates a label incorporating a two-element resonator wire in which energy may be transferred bidirectionally between adjacent resonators in the wire. Such bidirectional energy transfer could be accomplished by selecting the resonators in the wire such that the emission spectrum of the first mediating resonator significantly overlaps with the excitation spectrum of the second mediating resonator, and vice versa. This could be achieved by selecting the same fluorophore (e.g., ALEXA FLUORO® 594) for both of the mediating resonators in the wire.

Alternatively, one or more pairs of mediating resonators in a resonator network (e.g., adjacent resonators in a resonator wire) could be specified such that energy generally travels unidirectionally between pairs of such resonators.

FIG. 3B illustrates a schematic of an example label 300b that includes such a resonator pair. The example label 300b includes an input resonator ("IN"), two mediating resonators ("M1" and "M2"), and an output resonator ("OUT"). The relative probability of the different energy transfers between the resonators are indicated in FIG. 3B by the relative line weight of their representative arrows. Thus, for the example label 300b, it is more likely that the input resonator transfers energy to the first mediating resonator (M1) than vice versa. It is also more likely that the first mediating resonator (M1) transfers energy to the second mediating resonator (M2) than vice versa and more likely that the second mediating resonator (M2) transfers energy to output resonator than vice versa. Thus, energy generally travels unidirectionally from the input resonator through the mediating resonators to the output resonator. The temporal decay profile of such a label 300b could exhibit a narrower and/or less-delayed peak and/or could exhibit an overall reduced average delay relative to the temporal decay profile of the first example label 300a.

A label as described herein could include multiple resonator wires (e.g., multiple resonator wires of similar or different composition connected between common input and output resonators) having arbitrary lengths and/or compositions. For example, FIG. 3C illustrates a schematic of an example label 300c that includes a resonator wire of arbitrary length (i.e., that includes "n" resonators). The example label 300c includes an input resonator ("IN"), "n" mediating resonators ("M1," "M2," "M3," "M4, . . . " and "Mn"), and an output resonator ("OUT"). As indicated in FIG. 3C by the relative line weight of the representative arrows, energy transfers between adjacent mediating resonators in the resonator wire are bidirectional. However, one or more of the transitions between pairs of resonators of such a resonator wire could be unidirectional.

The resonator network of a label as described herein could represent different topologies, e.g., a branched topology. Such a branched topology could include multiple different resonator wires whose ends are connected to input resonators, output resonators, mediating resonators (e.g., an end resonator of one or more other resonator wires), or connected in some other way to provide a label exhibiting a desired temporal decay profile.

FIG. 3D illustrates a schematic of an example label 300d that includes two paths by which energy can travel through the resonator network to be emitted by an output resonator. The example label 300d includes an input resonator ("IN"), a first mediating resonators ("M1") that can receive energy from the input resonator and that can transmit energy to the output resonator, and three additional resonators ("M2," "M3," and "M4") arranged as a resonator wire that can transmit energy from the input resonator to the output resonator. As indicated by the relative line weight of the representative arrows, energy transfers between adjacent mediating resonators in the resonator wire are bidirectional. Such a resonator network could exhibit a temporal decay profile that is a mixture of other temporal decay profiles, e.g., that is a mixture of a first temporal decay profile of a label that only included the input, output, and first resonators and a second temporal decay profile of a label that only included the input, output, and resonator wire (i.e., mediating resonators "M2," "M3," and "M4"). A resonator network could include a two- or three-dimensional field of mediating resonators, input resonators, and/or output resonators. Such an arbitrary resonator network could be determined via a genetic algorithm or other automated process to provide a desired temporal decay profile or to satisfy some other criteria.

The resonator network of a label as described herein could include multiple input resonators and/or multiple output resonators. Such multiple input and/or output resonators could be provided to provide a variety of benefits, e.g., to adjust an effective temporal decay profile of the label, to increase a probability that the label is excited in response to illumination and/or to increase the effective brightness of the label, to provide wavelength-dependent multiplexing to the excitation and/or detection of the label (e.g., by causing the label to exhibit a different temporal decay profile, depending on which of a number of spectrally-distinct input resonators is excited), or to provide some other benefits. Multiple input resonators could be the same (that is, could each include the same fluorophores, quantum dots, or other optical elements) or could differ (e.g., could be different fluorophores such that the different input fluorophores are excited by respective different wavelengths of light). Multiple output resonators could be the same (that is, could each include the same fluorophores, quantum dots, or other optical elements) or could differ (e.g., could be different fluorophores such that the different output fluorophores emit light at respective different wavelengths). Additionally or alternatively, a single instance of a label could include multiple distinct or inter-connected resonator networks (e.g., multiple copies of the same resonator network) in order to increase and/or control the effective brightness of the label, to reduce a time and/or number of light pulses necessary to identify the label, or to provide some other benefit.

FIG. 3E illustrates a schematic of an example label 300e that includes an input resonator ("IN"), two mediating resonators ("M1" and "M2"), and a first output resonator ("OUT1"). The label additional optionally includes second ("OUT2") and third ("OUT3") output resonators. The additional output resonators could be provided to adjust a temporal decay profile of the label 300e. For example, the second output resonator could be the same as the first output resonator (e.g., could have the same emission spectrum) and could be added to the label 300e to increase a probability that the label 300e emits energy subsequent to the second mediating resonator being excited (e.g., by doubling the probability that energy from the second mediating resonator is transferred to one of the first or second output resonators such that one of the output resonators may then emit the received energy as a photon).

Additionally or alternatively, additional output resonators could differ with respect to emission wavelength or emission spectrum and could be provided to facilitate spectrally multiplexed detection of temporal decay profiles at different wavelengths corresponding to the different output resonators. For example, the third output resonator could differ from the first output resonator (e.g., could have a different emission spectrum) and could be added to the label 300e such that the label 300e could emit a photon from one or the other of the output resonators. Such photons, differing with respect to wavelength, could be separately detected and used to determine two different temporal decay profiles for the label 300e (or from a sample containing the label) and such multiple detected temporal decay profiles could be used to identify the label 300e.

FIG. 3F illustrates a schematic of an example label 300f that includes a first input resonator ("IN1"), two mediating resonators ("M1" and "M2"), and an output resonator ("OUT"). The label additional optionally includes second ("IN2") and third ("IN3") input resonators. The additional input resonators could be provided to adjust a temporal decay profile of the label 300f or to increase the probability that the label 300f is excited by exposure to illumination. For example, the second input resonator could be the same as the first input resonator (e.g., could have the same excitation spectrum) and could be added to the label 300f to increase a probability that the label 300f receives energy in response to illumination (e.g., by doubling the probability that a photon of the illumination is absorbed by at least one of the first or second input resonators).

Additionally or alternatively, additional input resonators could differ with respect to excitation wavelength or excitation spectrum and could be provided to facilitate spectrally multiplexed excitation of the label 300f and thus to facilitate spectrally multiplexed detection of temporal decay profiles at different wavelengths corresponding to the different input resonators. For example, the third input resonator could differ from the first input resonator (e.g., could have a different excitation spectrum) and could be added to the label 300f such that the label 300f could be excited, during first and second periods of time, by first and second illumination which differ with respect to wavelength and which are provided during the first and second periods of time, respectively. Such excitations of the label 300f, differing with respect to the input resonator by which the label 300f was excited, could be characterized by respective different temporal decay profiles and thus detected, during separate periods of time, and used to determine two different temporal decay profiles for the label 300f (or from a sample containing the label) and such multiple detected temporal decay profiles could be used to identify the label 300f.

Note that the resonator networks of the labels described herein may also be employed to generate samples of a random variable. The sample of the random variable may be generated based on a difference in time between excitation of the resonator networks/labels and a timing of detection of one or more photons responsively emitted from the resonator networks/labels. The particular distribution of the random variable could be related to the temporal decay profile of the resonator networks/labels. For example, the value of the generated sample could be a function of a detected time difference between a timing of illumination of the resonator network(s) and the timing of detection of one or more photons responsively emitted from the resonator network(s). A distribution of the generated random variable could be related to the temporal decay profile of the resonator network(s) and the function applied to generate samples of the random variable from the detected time difference. The structure of the resonator network(s) could be specified (e.g., to exhibit a particular temporal decay profile or other time-dependent probability density function) such that the function to generate samples from detected time differences is computationally tractable and/or efficient to compute.

III. Example Systems and Methods for Identifying Labels in a Sample

It can be beneficial in a variety of applications to interrogate a sample (e.g., a biological sample, or a stream of cells in a flow cytometer) or some other environment of interest in order to detect the presence, identity, absolute or relative amount, or other properties of labels as described herein that may be present in the sample or other environment of interest. Such interrogation could facilitate imaging of a sample, e.g., to determine the location, concentration, or other information about one or more analytes that are present within the sample and to which one or more varieties of labels are configured to bind. Such interrogation could facilitate the identification of cells, proteins, strands of RNA, or other contents of a sample in order to sort such contents or to provide some other benefit. For example, a flow cytometry apparatus could include a flow channel through which cells (or other particles of interest) flow. Such a flow channel could be interrogated as described herein in order to identify one or more labels in the channel and/or to identify the type or subtype of the cells, to determine a property of the cells, or to determine some other information based on the identified labels. Such information could then be used to sort the cells, e.g., according to cell type.

Such methods for detecting and/or identifying labels in an environment of interest could include providing illumination to the environment of interest (e.g., in the form of one or more ultrashort pulses of illumination) and detecting one or more properties of photons emitted from the environment in response to the illumination (e.g., a wavelength or spectrum of such photons, a timing of emission of such photons relative to a timing of the illumination, e.g., of one or more pulses of the illumination). This could include providing a single pulse of illumination and detecting the photons responsively emitted from a plurality of instances of one or more labels in the environment. Additionally or alternatively, one or more instances of one or more labels could be illumination a plurality of times by a plurality of pulses of illumination and the timing, relative to the pulses of illumination, of responsively emitted photons could be detected. Information about the timing of the responsively emitted photons could then be used to identify one or more labels that are present in the environment, to determine a binding state or other properties of such labels, to determine absolute or relative amounts of the label(s) in the environment, or to determine some other information related to one or more labels as described herein that are present in the environment.

Illumination could be provided to an environment as one or more pulses of illumination. The provided illumination could have a specified wavelength, e.g., an excitation wavelength of an input resonator of one or more of the labels. Such an excitation wavelength could be common across some or all of the labels present in the environment of interest, e.g., due to some or all of the labels including the same fluorophore, quantum dot, dye, or other optical substance or structure as their input resonator(s). Additionally or alternatively, multiple different wavelengths of light could be provided to excite multiple different input resonators, e.g., of multiple different labels. In some examples, such different wavelengths of light could be provided at different points in time (e.g., as part of different pulses of illumination) to facilitate spectrally-multiplexed detection of multiple different labels and/or multiple different sets of labels. In some examples, a single label could include multiple different input resonators, and the different input resonators could be excited by light at respective different wavelengths, e.g., as part of respective different pulses of illumination.

In order to improve the identification of labels in an environment, pulses of illumination used to interrogate the environment could be ultrashort pulses (e.g., pulses having durations on the order of attoseconds to nanoseconds). Such ultrashort pulses could be provided as broadband pulses emitted from a mode-locked oscillator. In examples wherein a label includes resonators having long-lifetime states (e.g., lanthanide atoms or other lanthanide compounds or complexes), the pulses of illumination could have longer durations, e.g., on the order of microseconds.

The timing, relative to such a pulse of illumination, of emission of photons from the environment in response to the pulse of illumination could be detected in a variety of ways. In some examples, the timing of individual photons could be detected, e.g., using one or more single-photon avalanche diodes, photomultipliers, or other single-photon detectors. The outputs of such detectors could be used, as part of a time-correlated single photon counter, to determine a count of photons determined as a function of time after a pulse of illumination is provided to the environment. The timing of such detected photons could be used to determine a probability density function for the timing of emission of photons from the sample in response to illumination of the sample.

Additionally or alternatively, detecting the timing of emission of photons from the environment could include detecting a timing of one or more peaks in the rate or intensity of the emitted photons, or detecting some other aggregate property of the timing of the emitting photons (e.g., to determine a delay timing of a peak of the rate of emission of photons that could be matched to the delay of a corresponding peak of a known temporal decay profile). Such detection could include applying a peak detector, a differentiator, a matched filter, or some other analog or digital signal processing techniques to the output of a single-photon avalanche diode or other photodetector element that is configured to receive photons emitted from the environment of interest.

One or more known labels could be present in an environment of interest and it could be beneficial to determine the identity of such labels and/or to determine some other information about the labels in the environment. As described above, such labels could be distinguished according to their temporal decay profiles; that is, each known label could be characterized by a respective different temporal decay profile. Thus, the identity of the one or more labels present in the environment could be determined by comparing the detected timing of emission of photons from the environment to a dictionary of temporal decay profiles, where each of the temporal decay profiles in the dictionary corresponds to a respective known label that could be present in the environment.

Figure 4A:
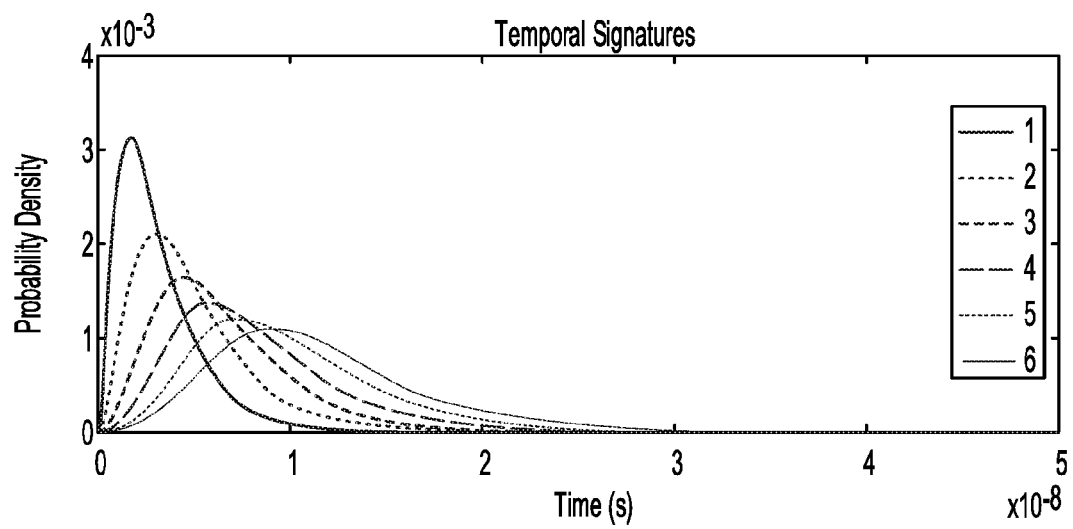
FIG. 4A shows the probability that a variety of different labels will emit a photon as a function of time following excitation of the labels.

FIG. 4A shows six different temporal decay profiles, each corresponding to one of six known labels. Each of the known labels has the same input resonator (e.g., ALEXA FLUORO® 430,) and output resonator (e.g., ALEXA FLUORO® 750) which form a resonator wire in combination with one or more of the same mediating resonator (e.g ALEXA FLUORO® 594). The known labels differ with respect to the number of mediating resonators. Information about the timing of photons received from an environment could be compared to the temporal decay profiles and used to determine which, if any, of the known labels are present in the environment. This could include comparing a delay of a peak rate of emission of photons from the environment to a delay of the peak in each of the known temporal decay profiles.

Figure 4B:
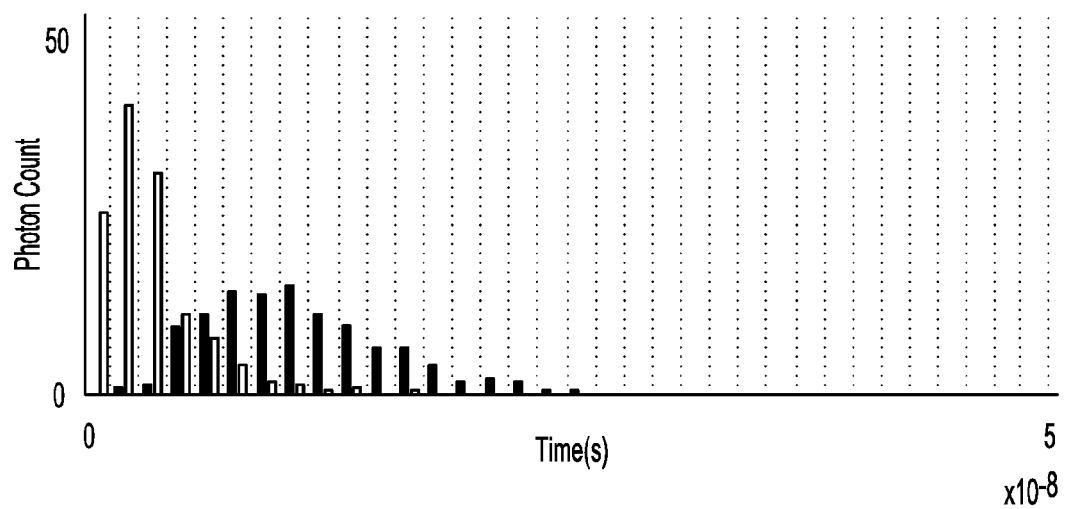
FIG. 4B shows the count of photon received from samples of two different labels as a function of time following excitation of the labels.

Additionally or alternatively, the detected timing of emission of photons could be used to determine a probability density function for the timing of emission of photons from the sample in response to illumination of the sample. Such a determined probability density function could then be compared to the temporal decay profiles of the known labels and used to identify one or more labels present in the environment. FIG. 4B illustrates the counts of photons detected from two different samples over time in a number of discrete ranges of time relative to illumination of the samples (at time 0). First counts (illustrated by the black rectangles) were received from a first sample that contained known label "6" from FIG. 4A, and second counts (illustrated by the white rectangles) were received from a second sample that contained known label "1" from FIG. 4A. The counts could be used to determine respective first and second probability density functions for the first and second samples, and the first and second probability density functions could be compared to the six known temporal decay profiles in order to identify which of the known labels are present in each of the samples. Such a comparison could include determining a measure of statistical divergence (e.g., a Kullback-Leibler divergence, a Jensen-Shannon divergence, a Bregman divergence, or a Fisher information metric) between a determined probability density function and each of the known temporal decay profiles. The label present in a sample could then be determined, e.g., by selecting the known label corresponding to the least of the determined measures of statistical divergence.

Similar or different methods could be used to determine whether multiple labels are present in a sample, and if so, to identify such multiple labels. In some examples, the identity of a cell or other contents of an environment (e.g., of a flow channel of a flow cytometry apparatus) could then be determined based on the identity of the labels in the environment, e.g., based on the determination that all of a subset of known labels are simultaneously present in a flow channel or other environment of interest.

In order to determine how many of a set of known labels are present in an environment, and to identify such present labels, a variety of methods can be used. For example, an expectation maximization algorithm can be used, in concert with a statistical mixture model, to determine the most likely labels present in an environment based on a determined probability density function for the timing of emission of photons from the environment in response to illumination of the environment. Such a mixture model could be based on the set of temporal decay functions corresponding to the set of known labels. Such an expectation maximization algorithm and mixture model could also be used to determine the relative amounts of such multiple labels in the sample.

Interrogating an environment could include detecting the timing of emission of photons within multiple different ranges of wavelengths. This could be done to detect the timing of emission of photons from two different output resonators of a label. Additionally or alternatively, this could be done to detect the timing of emission of photons from an output resonator, one or more mediating resonators, and/or an input resonator of the label.

Yet further, one or more of the labels present in the environment may include dark-state-exhibiting resonators such that the temporal decay profile of the labels is dependent on whether the dark-state-exhibiting resonators are in their respective dark states. For example, a label could include a first dark-state-exhibiting resonator and could exhibit a first temporal decay profile when the first dark-state-exhibiting resonator is in its dark state and the label could exhibit a second temporal decay profile when the first dark-state-exhibiting resonator is not in its dark state. In such examples, detection and/or identification of the label could include detecting a timing of optical excitation and re-emission during a time period when the dark-state-exhibiting resonator(s) is not in its dark state and, during a different period of time, inducing the dark-state-exhibiting resonator(s) to enter the dark state (e.g., by providing illumination at an excitation wavelength of the dark-state-exhibiting resonator(s)) and again detecting a timing of optical excitation and re-emission of the label.

IV. Example Resonator Networks

Resonator networks (e.g., resonator networks included as part of labels) as described herein can be fabricated in a variety of ways such that one or more input and/o readout resonators, output resonators, dark-state-exhibiting "logical input" resonators, and/or mediating resonators are arranged according to a specified network of resonators and further such that a temporal decay profile of the network, a brightness of the network, an excitation spectrum, an emission spectrum, a Stokes shift, or some other optical property of the network, or some other detectable property of interest of the network (e.g., a state of binding to an analyte of interest) corresponds to a specification thereof (e.g., to a specified temporal decay profile, a probability of emission in response to illumination). Such arrangement can include ensuring that a relative location, distance, orientation, or other relationship between the resonators (e.g., between pairs of the resonators) correspond to a specified location, distance, orientation, or other relationship between the resonators.

This can include using DNA self-assembly to fabricate a plurality of instances of one or more resonator networks. For example, a number of different DNA strands could be coupled (e.g., via a primary amino modifier group on thymidine to attach an N-Hydroxysuccinimide (NHS) ester-modified dye molecule) to respective resonators of a resonator networks (e.g., input resonators, output resonator, and/or mediator resonators). Pairs of the DNA strands could have portions that are at least partially complementary such that, when the DNA strands are mixed and exposed to specified conditions (e.g., a specified pH, or a specified temperature profile), the complementary portions of the DNA strands align and bind together to form a semi-rigid nanostructure that maintains the relative locations and/or orientations of the resonators of the resonator networks.

Figure 5:
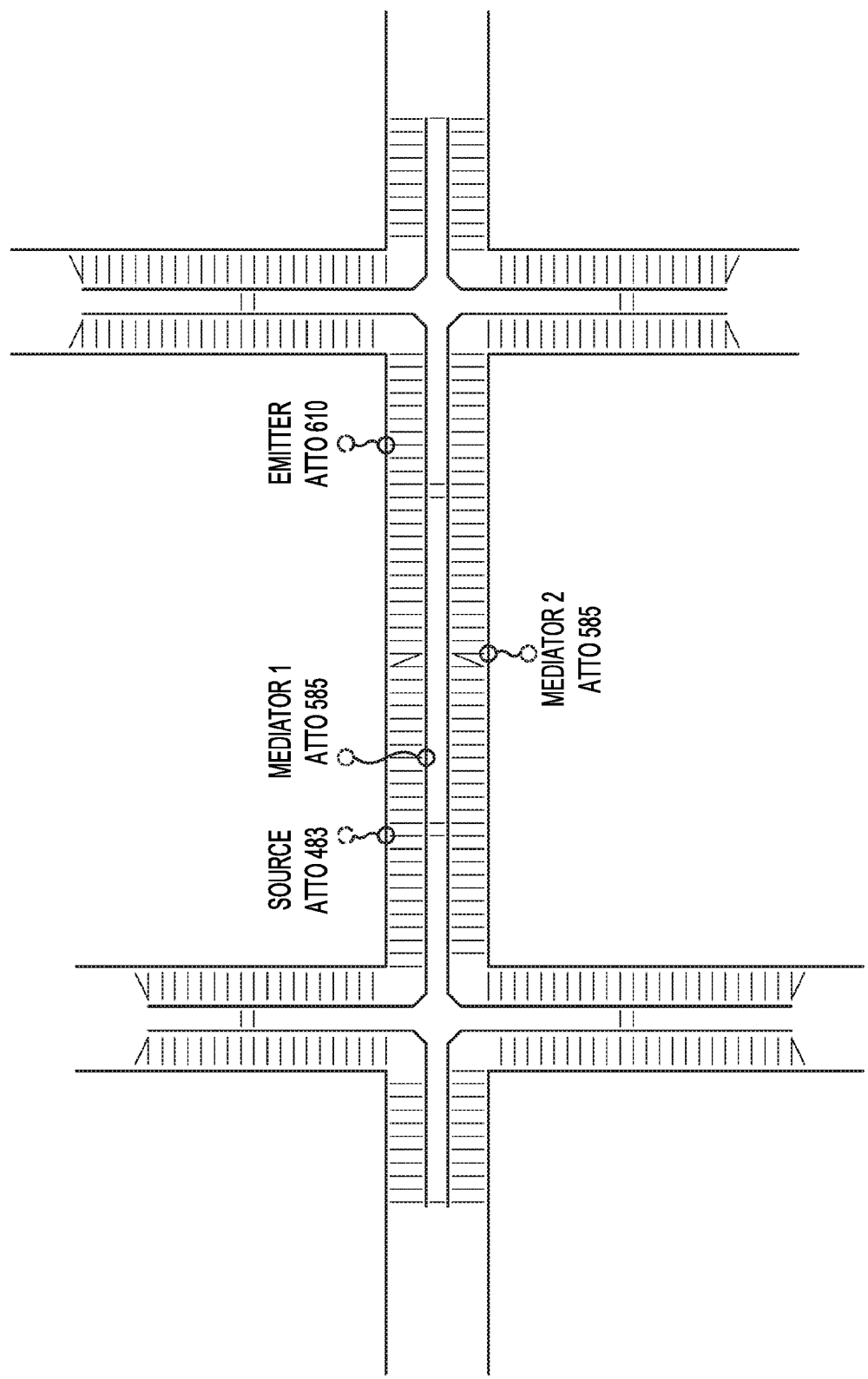
FIG. 5 shows a schematic of an example label.

FIG. 5 shows a schematic of such a resonator networks. An input resonator ("SOURCE ATTO 488"), an output resonator ("EMITTER ATTO 610) and two mediator resonators ("MEDIATOR 1 ATTO 565" and "MEDIATOR 2 ATTO 565") are coupled to respective DNA strands. The coupled DNA strands, along with additional DNA strands, then self-assemble into the illustrated nanostructure such that the input resonator, mediator resonators, and output resonator form a resonator wire. In some examples, a plurality of separate identical or different networks could be formed, via such methods or other techniques, as part of a single instance of a resonator network (e.g., to increase a brightness of the resonator network).

The distance between resonators of such a resonator network could be specified such that the resonator network exhibits one or more desired behaviors (e.g., is excited by light at a particular excitation wavelength and responsively re-emits light at an emission wavelength according to a specified temporal decay profile). This can include specifying the distances between neighboring resonators such that they are able to transmit energy between each other (e.g., bidirectionally or unidirectionally) and further such that the resonators do not quench each other or otherwise interfere with the optical properties of each other. In examples wherein the resonators are bound to a backbone via linkers (e.g., to a DNA backbone via an amide bond (created, e.g., by N-Hydroxysuccinimide (NHS) ester molecules) or other linking structures), the linkers could be coupled to locations on the background that are specified with these considerations, as well as the length(s) of the linkers, in mind. For example, the coupling locations could be separated by a distance that is more than twice the linker length (e.g., to prevent the resonators from coming into contact with each other, and thus quenching each other or otherwise interfering with the optical properties of each other). Additionally or alternatively, the coupling locations could be separated by a distance that is less than a maximum distance over which the resonators may transmit energy between each other. For example, the resonators could be fluorophores or some other optical resonator that is characterized by a Förster radius when transmitting energy via Förster resonance energy transfer, and the coupling locations could be separated by a distance that is less than the Förster radius.

V. Labels Using Specified Resonator Networks for Improved Brightness and/or Spectral Multiplexing When designing or specifying a set of resonator networks and/or labels for flow cytometry, molecular imaging, optical computation, biosensing, analyte assays, optical random number generation, or some other application (e.g., via a process of panel design), it can be beneficial to be able to arbitrarily select the excitation spectrum/wavelength, emission spectrum/wavelength, extinction coefficient, brightness, or other optical properties of one or more resonator networks. A combination of such resonator-network-containing labels (e.g., a contrast agent that includes two or more such labels) could then be applied to a sample in order to detect, identify, image, or otherwise observe respective analytes of interest in a sample (e.g., by mixing or otherwise applying the multi-label contrast agent to the sample). The ability to detect, distinguish, or otherwise observe such labels in a sample could be improved by selecting respective excitation wavelengths, emission wavelengths, brightnesses, extinction coefficients, absorption cross-sections, or other optical properties of the different labels applied to the sample. Such labels can be created, as described herein, to differ with respect to their excitation spectrum, their emission spectrum, their brightness, or other optical properties. This can be accomplished by specifying the identity, number, relative location and/or orientation, topology, or other properties of a network of resonators of the label.

For example, it can be beneficial to select and/or configure different labels to differ with respect to excitation wavelength, emission wavelength, Stokes shift, or other spectral properties in order to facilitate identification of such labels. Such identification could be based on a detected wavelength of light emitted therefrom and/or on a detected or determined brightness of light emission from the label as a function of the wavelength of light used to excite the label. However, when using single-resonator labels (e.g., single-fluorophore labels), the selection of such optical properties may be constrained by a limited library of commercially or otherwise available resonators. Using two-resonator labels (e.g., two-fluorophore labels configured such that one fluorophore acts as a donor and the other as an acceptor for Förster resonance energy transfer) may increase the space of potential labels and/or the range of possible optical properties thereof. However, such labels may still be limited (e.g., with respect to the magnitude of the effective Stokes shift of the label or other properties) by the availability of resonators having the desired optical properties that are also able to engage in energy transfer between each other (e.g., due to having sufficiently overlapping emission and excitation spectra).

In order to provide more freedom to specify such optical properties of a label and/or resonator network, the resonator network could include one or more mediating resonators configured to allow energy to be transferred, from an input resonator, to an output resonator via the one or more mediating resonators. In such resonator networks, the input resonator and output resonator may be selected (e.g., according to excitation spectrum/wavelength, emission spectrum/wavelength, brightness, compatibility with environmental conditions, tendency to photobleach) without the requirement that the output resonator be able to receive energy directly (e.g., via resonance energy transfer) from the input resonator. The one or more mediating resonators can then be selected and located within the resonator network, relative to the input and output resonators, such that energy received into the network as a result of the resonator network being illuminated may be transmitted to the output resonator via the mediating resonator(s).

Figure 6A:
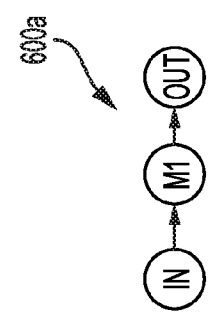
FIG. 6A shows a schematic of resonators in a label.

FIG. 6A illustrates a schematic of an example resonator network 600a as described herein. The example resonator network 600a includes an input resonator ("IN"), a mediating resonator ("M1"), and an output resonator ("OUT"). The input resonator can be excited by receiving illumination from the environment of the resonator network 600a (e.g., illumination at an excitation wavelength of the input resonator). The input resonator, output resonator, and mediating resonator are arranged such that the mediating resonator can receive energy from the input resonator and the output resonator can receive energy from the mediating resonator. The mediating resonator may be selected (e.g., from a set of commercially available fluorophores) such that it is able to receive energy from the input resonator and provide energy to the output resonator. This could include selecting the mediating resonator such that an emission spectrum of the input resonator overlaps with an excitation spectrum of the mediating resonator and/or such that an emission spectrum of the mediating resonator overlaps with an excitation spectrum of the output resonator.

Figure 6B:
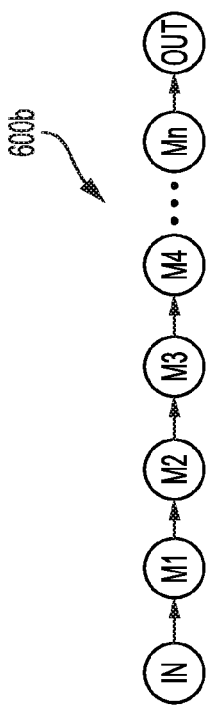
FIG. 6B shows a schematic of resonators in a label.

In order to permit a greater difference between the excitation spectrum/wavelength of the input resonator and the emission spectrum/wavelength of the output resonator of such a resonator network, the resonator network could include additional mediating resonators (e.g., disposed as a resonator wire within the label). FIG. 6B illustrates a schematic of an example resonator network 600b as described herein. The example resonator network 600b includes an input resonator ("IN"), n mediating resonators ("M1" through "M4" and "Mn"), and an output resonator ("OUT"). The input resonator can be excited by receiving illumination from the environment of the resonator network 600b (e.g., illumination at an excitation wavelength of the input resonator). The mediating resonators are arranged as a resonator wire or arbitrary length between the input resonator and the output resonator. That is, the n mediating resonators are arranged such that each resonator in the wire can receive energy from one neighboring resonator and transmit energy to another neighboring resonator. The number and identity of the resonators within such a resonator wire could be specified in order to adjust a difference between an excitation spectrum of the input resonator and an emission spectrum of the output resonator, e.g., to adjust a difference between an excitation wavelength of the input resonator and an emission wavelength of the output resonator. In such examples, each mediating resonator disposed between the input and output resonators could have an emission wavelength that is intermediate between an excitation wavelength of the input and an emission wavelength of the output resonator, e.g., such that transfer of energy to and/or from each mediating resonator permits a controlled reduction in the wavelength and/or magnitude of an exciton (or other quantum) of energy from the input resonator to the output resonator.

Further, it may be beneficial to increase or otherwise specify the brightness of labels and/or resonator networks as described herein in order to facilitate the detection or identification of such resonator networks. For example, different analytes of interest in a sample may be present in the sample at different concentrations or amounts. In such examples, the number or concentration of proteins, receptors, small molecules, segments of RNA, segments of DNA, or other analytes of interest present a sample (e.g., a sample containing cells that may be detected, identified, and/or sorted by a flow cytometry apparatus) may differ by a large amount (e.g., by multiple orders of magnitude). In such examples, applying a contrast agent that includes two labels, having approximately the same brightness, to the sample may result in the brightness of a first one of the labels, configured to bind to the more prevalent analyte, being much greater than the brightness of a second label, configured to bind to the less prevalent analyte, that is thus present in the sample at a lower concentration. The greater brightness, in the sample, of the first label may prevent or degrade the detection of the second label in the sample. In such an example, it can be beneficial to configure the second label to have a greater brightness than the first label. However, control over the brightness of such a label may be constrained by a limited library of commercially or otherwise available resonators (e.g., fluorophores).

Additionally, it can be generally beneficial to increase the brightness of resonator networks as described herein in order to facilitate the detection of rare analytes, to reduce an intensity of illumination necessary for such detection (e.g., to reduce photobleaching of the labels and/or to prevent damage to the sample due to such illumination), or to reduce an intensity of illumination necessary for some other application of the resonator networks (e.g., performance of optical logic functions, generation of samples of a random variable).

In order to increase or otherwise specify the brightness of such resonator networks (e.g., relative to other labels present in a contrast agent), a resonator networks could be configured to have multiple input resonators, output resonators, and/or resonator networks as described herein. The ability to control the brightness of such a resonator networks, or of multiple different resonator networks (e.g., respective different resonator networks of two or more labels present in a contrast agent used for flow cytometry, molecular imaging, or some other application) could facilitate panel selection for flow cytometry (e.g., by permitting the specification of greater brightness of labels corresponding to lower-abundance analytes in a sample relative to labels corresponding to more prevalent analytes) or other applications.

In order to control the brightness of a resonator network, DNA self-assembly or other techniques could be used to provide a resonator network having many instances of a single resonator, or of a number of resonators, such that the overall brightness of the resonator networks is increased by an amount related to the number of instances of the resonator. This could include providing many copies of a resonator network as described herein (e.g., 100, 300a-f, 600a-b) in order to increase the effective brightness of such a label, to reduce the number of photons detected therefrom and/or time (e.g., number of pulses of illumination) necessary to identify such labels, or to provide some other benefit. Such multiple resonators and/or multiple resonator networks could be located sufficiently far apart, within a label, such that substantially no energy transfer (e.g., resonance energy transfer) occurs between the resonators and/or resonator networks. Additionally or alternatively, the resonators and/or resonator networks could engage in energy transfer (e.g., to provide an increase in the brightness of the resonator networks via energy pooling or some other mechanism, or to provide some other benefit).

Figure 6C:
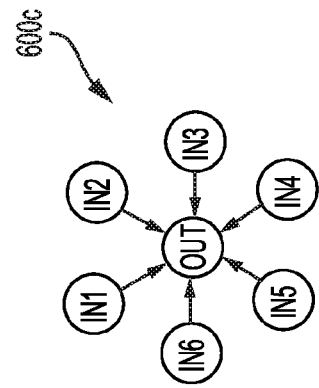
FIG. 6C shows a schematic of resonators in a label.

Additionally or alternatively, an absolute or relative number of input fluorophores and/or output fluorophores of a label and/or of a resonator network of a label could be specified to control the overall brightness of the resonator network. This could include specifying a resonator network such that one output resonator may receive energy (e.g., excitons) from a plurality of input resonators and/or such that a single input resonator may provide energy (e.g., excitons) to a plurality of output resonators. For example, FIG. 6C illustrates a schematic of an example resonator network 600c that includes six input resonators ("IN1" through "IN6") and an output resonator ("OUT"). As indicated by the representative arrows, energy transfers may occur from each of the input resonators directly to the output resonator. Such a resonator network could provide increased brightness by increasing the absorption cross-section of the resonator network, by providing additional sites that may be excited by illumination, or via some other mechanism or process.

Figure 6D:
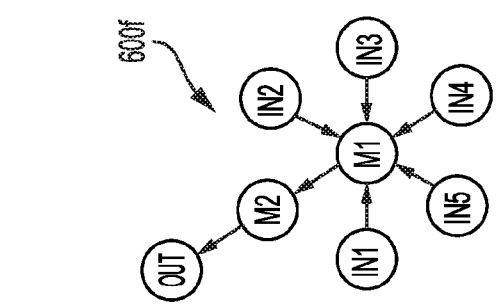
FIG. 6D shows a schematic of resonators in a label.

In another example, FIG. 6D illustrates a schematic of an example resonator network 600d that includes six output resonators ("OUT1" through "OUT6") and an input resonator ("IN"). As indicated by the representative arrows, energy transfers may occur to each of the output resonators directly from the input resonator. Such a resonator network could provide increased brightness in examples where energy transfer from the input resonator to the output resonator is improbable, where a time to emission of light by the output resonators (e.g., a fluorescence lifetime) is long, or via some other mechanism or process.

Figure 6E:
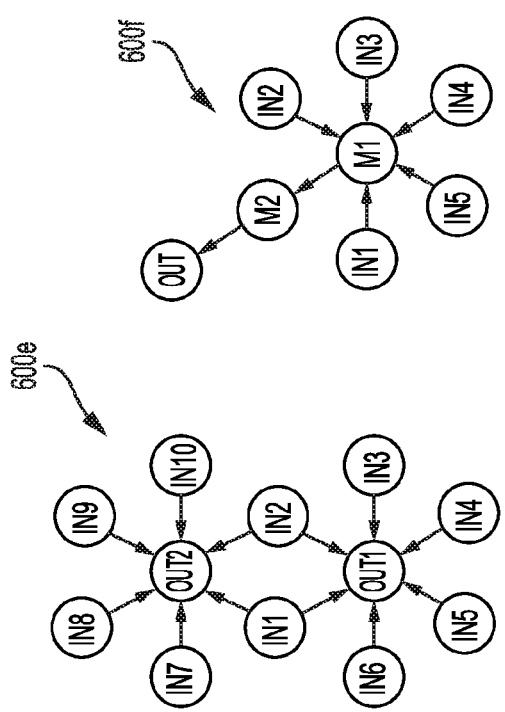
FIG. 6E shows a schematic of resonators in a label.

Note that resonator networks as described herein may include both input resonators that can provide energy to multiple output resonators and output resonators that can receive energy from multiple input resonators. For example, FIG. 6E illustrates a schematic of an example resonator network 600e that includes ten input resonators ("IN1" through "IN10") and two output resonators ("OUT1" and "OUT2"). As indicated by the representative arrows, energy transfers may occur from "IN1" and "IN2" directly to either of the output resonators. Energy transfers may also occur directly from "IN3" through "IN6" to "OUT1" and from "IN7" through "IN10" to "OUT2."

Figure 6F:
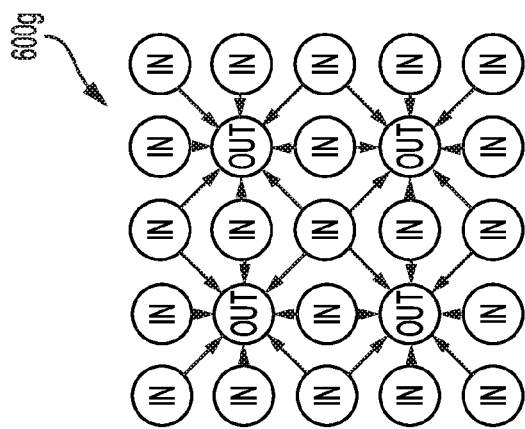
FIG. 6F shows a schematic of resonators in a label.

In some examples, a resonator network could include one or more mediating resonators (e.g., to increase a difference between an excitation wavelength of an input resonator and an emission wavelength of an output resonator, to adjust a temporal decay profile of the resonator network) to transfer energy from multiple input resonators to an output resonator and/or to transfer energy from an input resonator to multiple output resonators. FIG. 6F illustrates a schematic of an example resonator network 600f as described herein. The example resonator network 600f includes five input resonators ("IN1" through "IN5"), two mediating resonators ("M1" and "M2"), and an output resonator ("OUT"). The input resonators can be excited by receiving illumination from the environment of the resonator network 600f (e.g., illumination at an excitation wavelength of the input resonators).

The two mediating resonators are arranged as a resonator wire between the input resonators and the output resonator. That is, the two mediating resonators are arranged such that the first mediating resonator can receive energy from each of the input resonators, the second mediating resonator can receive energy from the first mediating resonator, and the output resonator can receive energy from the second mediating resonator. The number of resonators within such a resonator wire could be specified in order to adjust a temporal decay profile of the resonator network 600f (e.g., to adjust a delay or width of a peak in the decay profile, to increase an average decay of the decay profile, or to adjust some other property of the temporal decay profile), to increase a difference between an excitation wavelength of the input resonators and an emission wavelength of the output resonator, or to provide some other benefit.

The resonator network of a resonator network as described herein could represent different topologies, e.g., a branched topology. Such a branched topology could include multiple different resonator wires whose ends are connected to input resonators, output resonators, mediating resonators (e.g., an end resonator of one or more other resonator wires), or connected in some other way to provide a resonator network exhibiting a desired temporal decay profile.

Figure 6G:
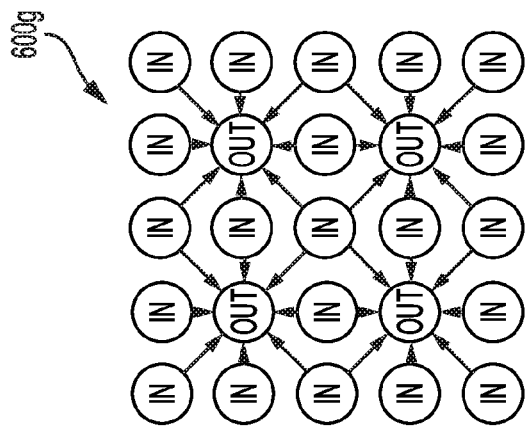
FIG. 6G shows a schematic of resonators in a label.

In some examples, a label and/or resonator network could include a plurality of input resonators, mediating resonators, and/or output resonators that are in some way interconnected to provide some or all of the benefits described herein. For example, FIG. 6G illustrates a schematic of an example resonator network 600g that includes a field of output resonators ("OUT") and input resonators ("IN"). As indicated by the representative arrows, energy transfers may occur to each of the output resonators directly from a number of input resonators and from each input resonator to one or more output resonators.

The brightness of such a resonator network, or of other resonator networks described herein (e.g., 600c, 600d, 600e, 600f) could be adjusted by controlling a ratio between a number of input resonators in the network and a number of output resonators in the network. For example, for certain input resonators, output resonators, and environmental conditions, a brightness of a resonator network could be increased by increasing a ratio between the number of input resonators and the number of output resonators (i.e., increasing the number of input resonators relative to the number of output resonators). Thus, the relative brightness of two labels comprising a contrast agent (e.g., a contrast agent used to stain a sample of cells for flow cytometry) could be adjusted by adjusting the ratios between input and output resonators of the two labels (e.g., such that a first ratio between input resonators and output resonators of the first label differs from a second ratio between input resonators and output resonators of the second label by a specified amount).

The brightness of a label and/or resonator network could also be increased by providing a network of input resonators wherein energy received (e.g., from environmental illumination) by an input resonator of the network is transferred to an output resonator of the network via one or more additional input resonators. A field of such input resonators could act to increase the absorption cross-section of the resonator network by effectively absorbing a significant fraction of photons that intersect with a planar shape and/or three-dimensional volume defined by the field of input resonators. Further, the input resonators could exhibit bidirectional energy transfer (e.g., pairs of neighboring input resonators could be capable of transferring energy between themselves in either direction), allowing the field of resonators to exhibit pooling of absorbed energy. Such pooling can increase the probability that photons intersecting the field are absorbed and/or increase the probability that energy absorbed by the field are successfully transferred, via the overall resonator network, to an output resonator. Such a resonator network could include many input resonators per output resonator, e.g., more than four input resonators per output resonator, or more than thirty input resonators per output resonator. The input resonators of such a field of input resonators could all be the same type of input resonator (e.g., the same type of fluorophore, having excitation and emission spectra that overlap such that different instances of the fluorophore can transmit energy between each other) or different types of resonators (e.g., to permit absorption of photons at multiple different excitation wavelengths or to provide some other benefit).

For example, FIG. 6H illustrates a schematic of an example resonator network 600h that includes an output resonator ("OUT") and a field of input resonators ("IN"). As indicated by the representative arrows, energy transfers may occur, bidirectionally, between neighboring input resonators. Additionally, energy transfer may occur to the output resonator directly from a number of neighboring input resonators. Accordingly, the output resonator may receive energy indirectly from non-neighboring input resonators via energy transmission through intermediary input resonators.

VI. Example Logical Resonator Networks

Resonator networks as described here (e.g., that are part of labels, that are used to generate random number generators) may be configured to exhibit behaviors that are optically modulatable or otherwise controllable. In some examples, the network behavior could be optically controllable, allowing the network to perform logical operations or to provide some other benefits. Such optical control could be provided for by one or more resonators of the network having an optically-induceable "dark state," wherein the resonator is unable, or less able, to transmit and/or receive energy (e.g., excitons) when in the dark state. Additionally or alternatively, the behavior of a resonator network could be related to a property of the environment of the network (e.g., to a pH level, to the binding of an analyte of interest to the network), permitting the resonator network to be used to optically detect the property of the environment of the network. In some examples, a single resonator network could include both sensor behaviors and optically-controllable behaviors, allowing a single resonator network to be optically controlled to detect multiple different analytes or other environmental variables (e.g., by operating optical logic elements of the network to "address" a particular sensed variable of interest).

Optical control of resonator network behavior can be provided via a variety of methods. In some examples, the state of individual resonators may be optically adjusted. This may be performed irreversibly, e.g., by photobleaching one or more resonators by illuminating the resonators with illumination at an excitation wavelength of the resonator(s) at an intensity above a threshold level. Alternatively, the state of individual resonators may be reversibly adjusted, e.g., by optically inducing the resonator(s) to enter a "dark state."

A "dark state" is a state wherein a resonator (e.g., a fluorophore, a quantum dot, or some other optically active molecule or atom as described herein) become incapable, or become less capable, of transmitting and/or receiving energy (e.g., photons, excitons) to and/or from the environment of the resonator (e.g., from other resonators of a resonator network). The resonator may be optically placed into the dark state by illumination by light at a particular wavelength. Such illumination may cause the resonator to enter the dark state by, e.g., causing an electron to transition into another energy state that prevents the resonator from absorbing additional energy, causing the resonator to gain/lose charge (e.g., to receive and/or donate an electron from/to the environment), or by causing the resonator to undergo some other process. Accordingly, a resonator network that includes one or more such resonators (i.e., resonators that may be optically controlled to enter a dark state) may have a temporal decay profile, a probability of photon re-emission following illumination, or some other property that is optically controllable by providing illumination sufficient to cause the resonator(s) to enter the dark state.

Such dark state resonators may be provided as part of a resonator network in order to allow for optical control of the flow of energy (e.g., excitons) through the network. Such a resonator network could be configured such that the dark state resonator, when in the dark state, acts to facilitate energy flow through the resonator network (e.g., from one portion of the network to another, and/or from an input of the network to an output of the network). Additionally or alternatively, a resonator network could be configured such that the dark state resonator, when in the dark state, acts to inhibit energy flow through the resonator network (e.g., from one portion of the network to another, and/or from an input of the network to an output of the network). Such optically-controllable inhibition and/or excitation can be used to provide logic gates, energy flow control within a resonator network, or a variety of other behaviors and/or applications.

A resonator that exhibits such an optically-inducible dark state may be applied in a variety of ways within a resonator network in order to, when in the dark state, inhibit energy flow through the resonator network. For example, such an inhibiting resonator may be provided as part of a path for energy flow within the resonator network. Accordingly, when the inhibiting resonator is in the dark state (e.g., due to illuminating the resonator network with light at an appropriate wavelength), energy flow along the path will be fully or partially prevented, thus fully or partially inhibiting energy flow along the path.

This is illustrated by way of example in FIGS. 7A and 7B, which illustrate an example resonator network 700a at respective different points in time. The resonator network 700a includes a readout resonator ("CLK"), an input resonator ("IN"), and an output resonator ("OUT"). When the input resonator is not in the dark state (illustrated in FIG. 7A), energy (e.g., excitons) may be transmitted from the readout resonator (e.g., in response to the readout resonator being illuminated by light 710a at an excitation wavelength of the readout resonator) to the input resonator, and from the input resonator to the output resonator. Thus, when the input resonator is not in the dark state, illumination 710a absorbed by the resonator network (by the readout resonator) may be transmitted through the resonator network 700a to the output resonator, and then emitted as a photon 720a from the output resonator.

Conversely, when the input resonator is in the dark state (illustrated, in FIG. 7B, by the "IN" resonator being drawn in dashed lines), energy (e.g., excitons) is unable to be transmitted from the readout resonator to the input resonator, and from the input resonator to the output resonator. Thus, when the input resonator is in the dark state, illumination 710a absorbed by the resonator network (by the readout resonator) is not transmitted through the resonator network 700a to the output resonator, which thus does not responsively emit a photon.

Additionally or alternatively, a resonator that exhibits such an optically-inducible dark state may be applied in a variety of ways within a resonator network in order to, when in the dark state, facilitate energy flow through the resonator network. For example, such a facilitating resonator may be provided as part of an alternative, dissipative and/or non-radiative path for energy flow within the resonator network. Such a facilitating resonator, which not in the dark state, could act to sink or otherwise preferentially receive energy (e.g., excitons), preventing the energy from traveling to an output resonator or other portion of the resonator network. Accordingly, when the facilitating resonator is in the dark state (e.g., due to illuminating the resonator network with light at an appropriate wavelength), energy will not flow to the facilitating resonator and thus may flow along a different path through the network (e.g., to an output resonator).

This is illustrated by way of example in FIGS. 7C and 7D, which illustrate an example resonator network 700b at respective different points in time. The resonator network 700b includes a readout resonator ("CLK"), an input resonator ("IN"), a mediating resonator ("M"), and an output resonator ("OUT"). When the input resonator is not in the dark state (illustrated in FIG. 7C), energy (e.g., excitons) may be transmitted from the readout resonator (e.g., in response to the readout resonator being illuminated by light 710b at an excitation wavelength of the readout resonator) to the mediating resonator, and from the mediating resonator to either of the input resonator or the output resonator. If transmitted to the input resonator, the energy is likely to be dissipated (e.g., lost from the network as heat, or emitted as a photon at an emission wavelength of the input resonator), while the energy, if transmitted to the output resonator, is likely to be emitted as a photon, at an emission wavelength of the output resonator, from the output resonator.

The relative probability of the different energy transfers between the resonators are indicated in FIGS. 7C and 7D by the relative line weight of their representative arrows. Thus, for the example network 700b, when the input resonator is not in the dark state, it is more likely that the mediating resonator transfers energy to the input resonator than to the output resonator. Thus, when the input resonator is not in the dark state, illumination 710b absorbed by the resonator network (by the readout resonator) is more likely to be absorbed, and then dissipated by, the input resonator than it is to be received by the output resonator and transmitted from the network 700b as a photon.

Conversely, when the input resonator is in the dark state (illustrated, in FIG. 7D, by the "IN" resonator being drawn in dashed lines), energy (e.g., excitons) is unable to be transmitted from the mediating resonator to the input resonator, and thus is transmitted to the output resonator. Thus, when the input resonator is in the dark state, illumination 710b absorbed by the resonator network (by the readout resonator) may be transmitted through the resonator network 700b to the output resonator, and then emitted as a photon 720b from the output resonator.

Such behavior may be employed to implement logic gates or other computational or gating functions in a resonator network as described herein. For example, the resonator network 700a illustrated in FIGS. 7A and 7B could be employed as a NOT gate, with "evaluation" of the gate triggered by excitation of the readout resonator. Detection of the gate output may be achieved by detecting whether the output resonator emitted a photon in response to the "evaluation." The gate input is applied by providing (or not providing) illumination at an input wavelength such that the input resonator enters the dark state. Accordingly, a "high" input (illumination sufficient to cause the input to enter the dark state) would result in a "low" output (the network not emitting a photon from the output resonator in response to excitation of the readout resonator). Conversely, a "low" input will result in a "high" output, providing the behavior of a NOT gate.

Resonator structures may be designed to provide arbitrary logic gate functions or other computational or gating functionality. This can include providing multiple "input" resonators, which may be caused to enter a dark state by providing illumination to the input resonators at an appropriate wavelength. These additional input resonators may differ with respect to the wavelength of light necessary to induce the dark state. These additional resonators may also differ with respect to whether they facilitate the flow of energy through the network or inhibit the flow of energy through the network. Accordingly, light provided (or not provided) at these different wavelengths may represent respective different logical inputs to the resonator network. The wavelengths may differ by more than a specified amount (e.g., by more than 10 nanometers, or by more than 50 nanometers) in order to permit reliable and independent signaling along the respective different logical inputs.

Figure 8A:
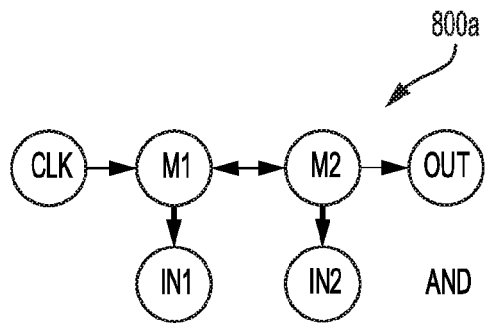
FIG. 8A shows a schematic of resonators in a network.

An example of such a resonator network, configured as a logical AND gate, is shown in FIG. 8A. The resonator network 800a includes a readout resonator ("CLK"), two mediating resonators ("M1" and "M2"), two input resonators ("IN1" and IN2"), and an output resonator ("OUT"). The relative probability of the different energy transfers between the resonators are indicated in FIG. 8A by the relative line weight of their representative arrows. Thus, in order for energy to be transmitted from the readout resonator to the output resonator with high probability, both of the input resonators must be in their dark states (e.g., in response to being provided with illumination at their respective input wavelengths).

Figure 8B:
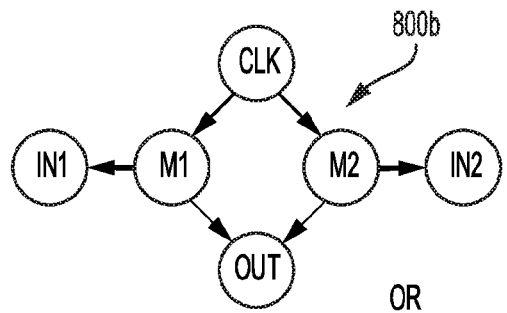
FIG. 8B shows a schematic of resonators in a network.

Another example of such a resonator network, configured as a logical OR gate, is shown in FIG. 8B. The resonator network 800b includes a readout resonator ("CLK"), two mediating resonators ("M1" and "M2"), two input resonators ("IN1" and IN2"), and an output resonator ("OUT"). The relative probability of the different energy transfers between the resonators are indicated in FIG. 8B by the relative line weight of their representative arrows. Thus, in order for energy to be transmitted from the readout resonator to the output resonator with high probability, at least one of the input resonators must be in its dark state (e.g., in response to being provided with illumination at one or both of their respective input wavelengths).

Figure 8C:
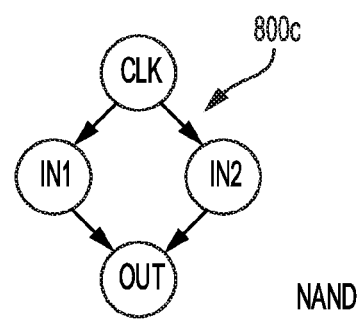
FIG. 8C shows a schematic of resonators in a network.

Another example of such a resonator network, configured as a logical NAND gate, is shown in FIG. 8C. The resonator network 800c includes a readout resonator ("CLK"), two input resonators ("IN1" and IN2"), and an output resonator ("OUT"). The relative probability of the different energy transfers between the resonators are indicated in FIG. 8C by the relative line weight of their representative arrows. Thus, in order for energy to be transmitted from the readout resonator to the output resonator with high probability, no more than one of the input resonators may be in its dark state (e.g., in response to being provided with illumination at one or the other, or neither, of their respective input wavelengths).

Figure 8D:
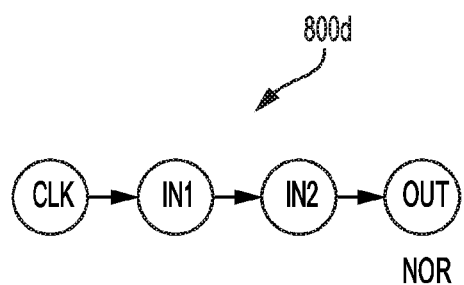
FIG. 8D shows a schematic of resonators in a network.

Another example of such a resonator network, configured as a logical NOR gate, is shown in FIG. 8D. The resonator network 800d includes a readout resonator ("CLK"), two input resonators ("IN1" and IN2"), and an output resonator ("OUT"). The relative probability of the different energy transfers between the resonators are indicated in FIG. 8D by the relative line weight of their representative arrows. Thus, in order for energy to be transmitted from the readout resonator to the output resonator with high probability, neither of the input resonators may be in their dark states (e.g., in response to being provided with illumination at neither of their respective input wavelengths).

Figure 8E:
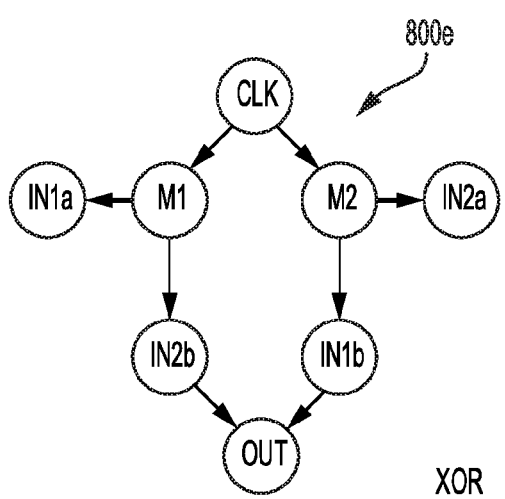
FIG. 8E shows a schematic of resonators in a network.

Multiple input resonators that enter their dark states in response to receiving illumination at the same wavelength may be provided in a single resonator network in order to achieve a specified logical function or behavior. An example of such a resonator network, configured as a logical XOR gate, is shown in FIG. 8E. The resonator network 800e includes a readout resonator ("CLK"), two mediating resonators ("M1" and "M2"), four input resonators ("IN1a," "IN1b," "IN2a," and IN2b"), and an output resonator ("OUT"). The relative probability of the different energy transfers between the resonators are indicated in FIG. 8E by the relative line weight of their representative arrows. Thus, in order for energy to be transmitted from the readout resonator to the output resonator with high probability, one and only one of the input resonators must be in their dark state (e.g., in response to being provided with illumination at one or the other, exclusively, of their respective input wavelengths).

Figure 8F:
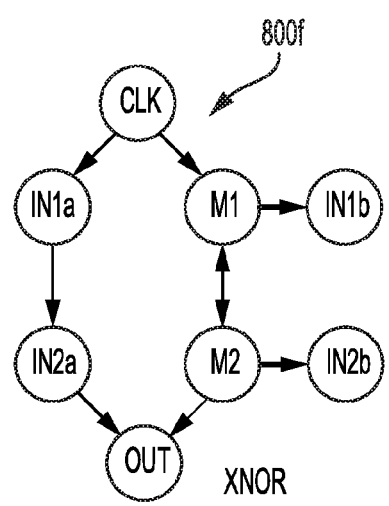
FIG. 8F shows a schematic of resonators in a network.

Another example of such a resonator network, configured as a logical XNOR gate, is shown in FIG. 8F. The resonator network 800f includes a readout resonator ("CLK"), two mediating resonators ("M1" and "M2"), four input resonators ("IN1a," "IN1b," "IN2a," and IN2b"), and an output resonator ("OUT"). The relative probability of the different energy transfers between the resonators are indicated in FIG. 8F by the relative line weight of their representative arrows. Thus, in order for energy to be transmitted from the readout resonator to the output resonator with high probability, either both or neither of the input resonators must be in their dark state (e.g., in response to being provided with illumination at both of their respective input wavelengths or at neither of their respective input wavelengths).

Figure 9A:
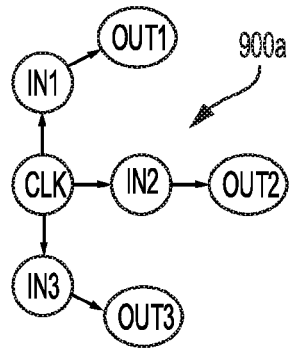
FIG. 9A shows a schematic of resonators in a network.

A resonator network may include input resonators as described herein (e.g., dark-state-exhibiting resonators whose dark state may be optically induced and/or otherwise optically controlled) to control the flow of energy through the resonator network (e.g., between different portions of the resonator network). Such inputs may be controlled in order to selectively activate or deactivate portions of the resonator network. This is illustrated by way of example in FIG. 9A, which shows a resonator network 900a that includes a readout resonator ("CLK"), three input resonators ("IN1," "IN2," and IN3"), and three output resonators ("OUT1," "OUT2," and "OUT3"). The relative probability of the different energy transfers between the resonators are indicated in FIG. 9A by the relative line weight of their representative arrows. Thus, in order for energy to be transmitted from the readout resonator to a particular one of the output resonators, the corresponding input resonator must not be in its dark state. Accordingly, the output resonator(s) that may emit photons in response to excitation of the readout resonator may by selected by providing (or not providing) illumination at the respective input wavelengths of the input resonators. For example, to select the "OUT1" output resonator, light could be provided at the dark-state-inducing wavelengths for the second ("IN2") and third ("IN3") input resonators.

Resonator networks that are optically-controllable (e.g., by optically inducing a dark state in one or more resonators of the networks) may be applied to provide a variety of benefits. For example, resonator network-containing labels as described herein may include such dark state resonators in order to provide further multiplexing for label detection and identification. This could include the label exhibiting a first temporal decay profile or other time-dependent probability density function with respect to the relative timing of emission of photons in response to illumination when an input resonator of the label is in a dark state. The label could then exhibit a second temporal decay profile or other time-dependent probability density function when the input resonator is not in the dark state. Accordingly, the label could be optically interrogated during the first and second periods of time, with the input resonator being not in the dark state during the first period of time and being in the dark state during the second period of time (e.g., due to illumination at an excitation wavelength of the input resonator). The detected relative timing of emission of light from the label, in response to illumination, during the first and second time periods could be used together to identify the label.

In another example, resonator networks as described herein may include such dark state resonators in order to provide a controllable time-dependent probability density function with respect to the timing of emission of photons from the resonator network(s) in response to illumination. The detected relative timing could be used to generate samples of a random variable, with the probability distribution of the random variable being related to the time-dependent probability density function exhibited by the resonator network(s). One or more input resonators of such a resonator network being in a dark state could modify the time-dependent probability density function exhibited by the resonator network(s). Accordingly, the probability distribution of the random variable samples generated therefrom could be controlled by controlling whether such input resonator(s) are in the dark state.

In some examples, this could include applying dark state input resonators within a resonator network to control whether sections of the resonator network are available to transfer energy from a readout resonator of the network to an output resonator of the network. Each such configuration of the network, including only the portions of the network "enabled" by the dark state of the input resonator(s), could correspond to a respective different time-dependent probability density function and thus be used to generate samples of a respective different random variable.

Figure 9B:
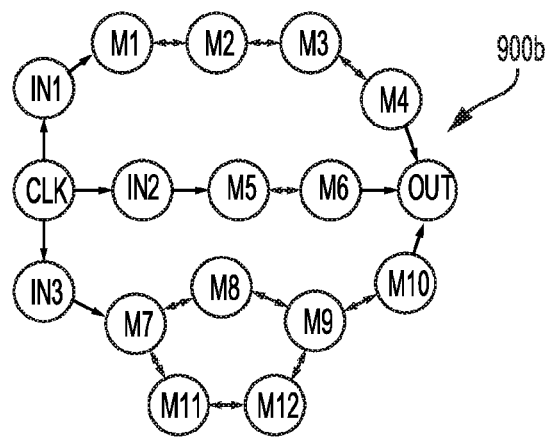
FIG. 9B shows a schematic of resonators in a network.

This is illustrated by way of example in FIG. 9B, which shows a resonator network 900b that includes a readout resonator ("CLK"), three input resonators ("IN1," "IN2," and IN3"), twelve mediating resonators ("M1" through "M12"), and an output resonator ("OUT"). The relative probability of the different energy transfers between the resonators are indicated in FIG. 9B by the relative line weight of their representative arrows. Thus, in order for energy to be transmitted from the readout resonator to the output resonator, at least one of the input resonators must not be in its dark state. The overall time-dependent probability density function exhibited by the resonator network 900b, with respect to the timing of emission of photons from the output resonator in response to excitation of the readout resonator, is related to whether each of the input resonators is or is not in its dark state. So, for example, if the "IN2" and "IN3" input resonators are in their dark state, and "IN1" is not in its dark state, the resonator network 900b will exhibit a time-dependent probability density function related to the resonator wire comprised of "IN1," "M1," M2," "M3," and "M4." In another example, if the "IN3" input resonator is in its dark state, and the "IN1" and "IN2" resonators are not in their dark states, the resonator network 900b will exhibit a time-dependent probability density function related to a combination of the time-dependent probability density function of the resonator wire comprised of "IN1," "M1," M2," "M3," and "M4" and an additional time-dependent probability density function related to the resonator wire comprised of "IN2," M5," and "M6."

In yet another example, resonator networks as described herein may include sensors for detecting properties of the environment of the resonator networks, e.g., a pH of a solution to which the resonator network is exposed, or the presence or amount of an analyte bound to a receptor of the resonator network. Such a resonator network could include a variety of sensor elements or other components (e.g., the resonators of the network itself) that are able to transduce a property of the environment of the network into an optically-detectable change in the resonator network (e.g., a change in an overall intensity or probability of light emission in response to illumination, a change in a temporal decay function and/or a time-dependent probability density function of light emission from the network in response to illumination). For example, one or more resonators of the resonator network may have an optical property (e.g., a property of being quenched, or of entering a dark state) that is related to a pH or other property of a solution to which the resonator is exposed, to whether the resonator has bound to an analyte of interest, or to some other property of interest in the environment of the resonator network.

In another example, such a sensor could comprise a receptor (e.g., an antibody, an aptamer, one or more proteins, a DNA or RNA strand) that preferentially binds to an analyte of interest (e.g., a protein, a hormone, a cell, a cell surface receptor or other cell surface element, a complementary DNA or RNA strand, a small molecule, a metal ion). The state of binding of such a receptor to the analyte of interest could then be related to one or more detectable optical properties of the resonator network in a variety of ways. For example, binding of the analyte to the receptor could result in a change of the relative location of one or more resonators within the resonator network, thus changing an optically detectable property of the resonator network (e.g., a overall intensity or probability of light emission in response to illumination, a change in a temporal decay function and/or a time-dependent probability density function of light emission from the network in response to illumination). Such a change could be due to a change in conformation of the receptor, to a change in conformation of one or more elements of a backbone of the resonator network, or to a change in location of a resonator or backbone element coupled to the receptor. Additionally or alternatively, the receptor could be coupled to and/or part of a resonator of the network (e.g., part of a protein that includes a fluorescent moiety) such that the receptor not being bound to an instance of the analyte causes the resonator to be quenched or otherwise optically disabled. Alternatively, the receptor being bound to an instance of the analyte could cause the resonator to be quenched or otherwise optically disabled.

Figure 10A:
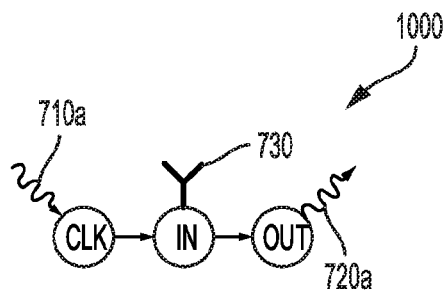
FIG. 10A shows a schematic of resonators in a network.
Figure 10B:
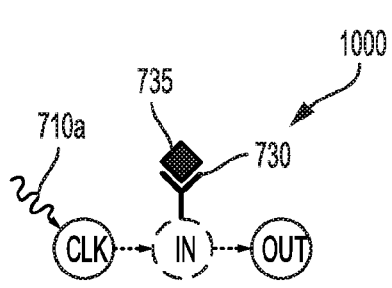
FIG. 10B shows a schematic of resonators in a network.

This is illustrated by way of example in FIGS. 10A and 10B, which illustrate an example resonator network 1000. The resonator network 1000 includes a readout resonator ("CLK"), a receptor 730 that preferentially binds to an analyte of interest 735, a mediating resonator ("IN") that is quenched when an instance of the analyte 735 is bound to the receptor 730, and an output resonator ("OUT"). Thus, when the receptor 730 is not bound to an instance of the analyte, the resonator network 1000 can emit light 720a in response to receiving light 710a at an excitation wavelength of the readout resonator (illustrated in FIG. 10A). Conversely, when the receptor 730 is bound to an instance of the analyte 735, the resonator network 1000 is unable to emit light in response to receiving light 710a at an excitation wavelength of the readout resonator, since the mediating resonator has been quenched and is thus unavailable to transmit received energy from the readout resonator to the output resonator (illustrated in FIG. 10B).

A resonator network that is configured, as described above, for optically sensing one or more properties of the environment of the resonator network may include one or more dark state exhibiting input resonators. Such input resonators could permit multiplexing of the resonator network in order to use the network to detect multiple different environmental properties. For example, a resonator could include multiple different receptors that selectively interact with respective different analytes and that, when bound to an instance of a respective analyte, quench a respective resonator of the network or otherwise induce a change in an optical property of a respective portion of the resonator network. One or more input resonators could be provided in such a resonator network, to permit optically-controlled multiplexing of analyte detection using the resonator network. This could include using the input resonators to implement logic gates or other means for addressing the sensors such that the resonator network response to a readout resonator being excited (e.g., an intensity or a timing of emission of light from an output resonator of the resonator network) is related to whether an optically-selected one of the receptors is bound to an instance of a corresponding analyte. Such optically-controlled multiplexing could also permit sub-wavelength imaging and/or analyte assays, by enabling the optical control and/or selection of different portions of a resonator network that are separated from each other by a distance that is less than an imaging wavelength.

VII. Example Methods

Figure 11:
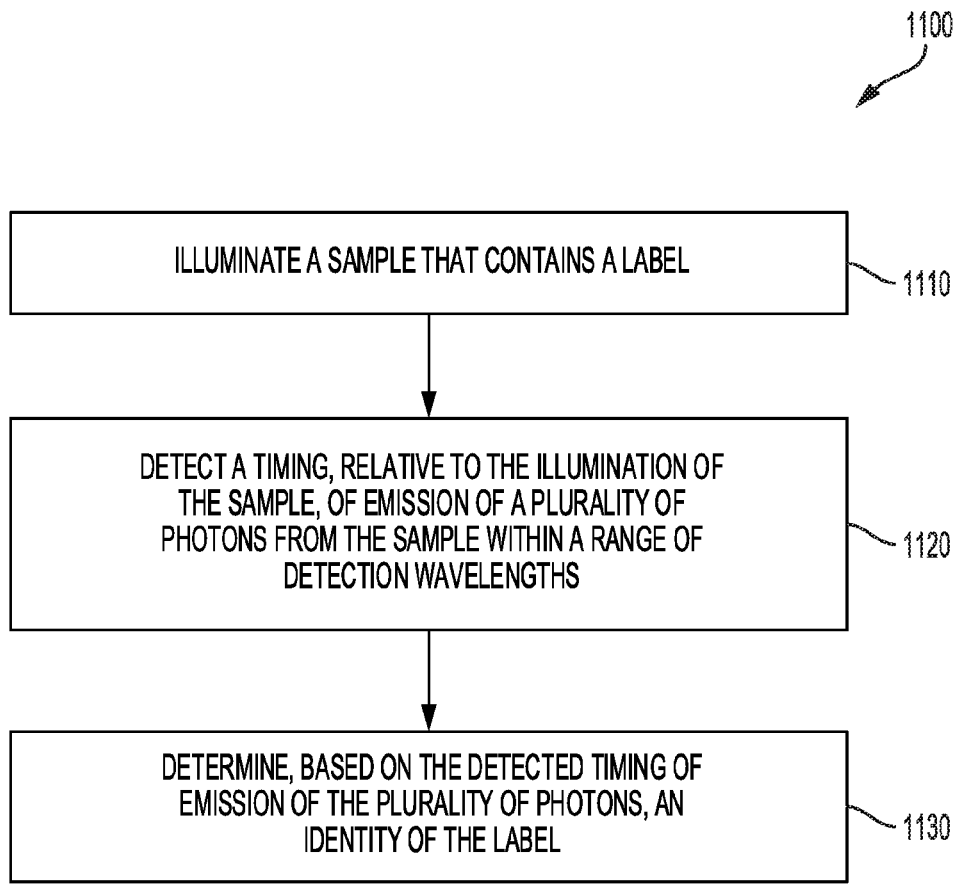
FIG. 11 shows a flow chart of an example method.

FIG. 11 is a flowchart of a method 1100 for interrogating a sample to detect and identify one or more labels, as described herein, that may be contained within the sample. For purposes of illustration, the label identified in method 1100 includes: (i) an input resonator; (ii) an output resonator that is characterized by an emission wavelength; and (iii) a network of one or more mediating resonators. The relative locations of the input resonator, the output resonator, and the one or more mediating resonators within the label are such that energy can be transmitted from the input resonator to the output resonator via the network of one or more mediating resonators in response to the input resonator being excited by illumination (e.g., by a pulse of laser light at an excitation wavelength of the input resonator).

The method 1100 includes illuminating a sample that contains the label (1110). This could include illuminating the sample with one or more pulses of illumination. Such pulses of illumination could be ultrashort pulses, having pulse widths between attoseconds and nanoseconds. The pulses of illumination could have different spectra and/or include different wavelengths of light. For example, a first pulse of illumination could include light at an excitation wavelength of the input resonator of the label and a second pulse of illumination could include light at an excitation wavelength of an input resonator of a different label. In another example, a first pulse of illumination could include light at an excitation wavelength of the input resonator of the label and a second pulse of illumination could include light at an excitation wavelength of a further input resonator of the label.

The method 1100 also includes detecting a timing, relative to the illumination of the sample, of emission of a plurality of photons from the sample within a range of detection wavelengths (1120). The range of detection wavelengths includes the emission wavelength of the output resonator of the label. Detecting the timing of emission of a plurality of photons from the sample could include detecting the timing of reception of individual photons, e.g., using a single photon avalanche diode, a photomultiplier tube, or some other detector element(s). Additionally or alternatively, detecting the timing of emission of a plurality of photons from the sample could include detecting a timing of a peak or other feature of the variation over time of the intensity, rate, or other property of the photons emitted from the sample.

The method 1100 further includes determining, based on the detected timing of emission of the plurality of photons, an identity of the label (1130). Determining the identity of the label includes selecting the identity of the label from a set of known labels. Determining the identity of the label could include comparing the detected timing of emission of the plurality of photons to a set of temporal decay profiles that correspond to the known labels. For example, the detected timing of emission of the plurality of photons could be used to determine a probability density function for the timing of emission of photons from the sample in response to illumination of the sample. Such a determined probability density function could then be compared to each of the known temporal decay profiles. Such a comparison could include determining a measure of statistical divergence between the probability density function and the known temporal decay profiles, e.g., a Kullback-Leibler divergence, a Jensen-Shannon divergence, a Bregman divergence, or a Fisher information metric.

The method 1100 could include additional or alternative steps as described elsewhere herein. For example, the method 1100 could include identifying a cell or other contents of the sample based on the determined identity of one or more labels in the sample. The method 1100 could include sorting cells or other particulates in the sample, based on the determined identity of the label (e.g., the sample could be contained within a flow channel of a flow cytometry apparatus, and cells in the flow chamber could be sorted according to the determined identity of one or more labels in the flow channel). The method 1100 could include emitting light at an excitation wavelength of a dark state-exhibiting resonator of the resonator wavelength, such that the temporal decay profile or other optically-detectable property of the label is adjusted, and identifying the label could include determining that the detected timing corresponds to the adjusted state of the optically-detectable property. The example method 1100 illustrated in FIG. 11 is meant as an illustrative, non-limiting example. Additional or alternative elements of the method are anticipated, as will be obvious to one skilled in the art.

Figure 12:
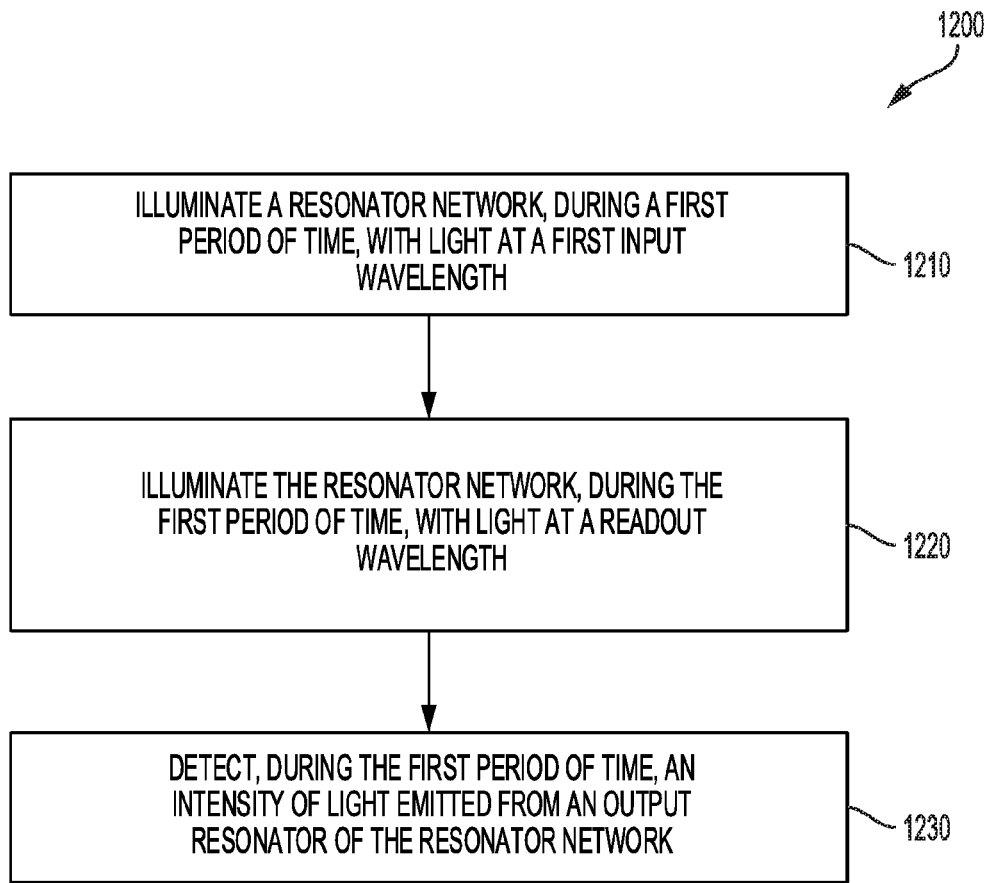
FIG. 12 shows a flow chart of an example method.

FIG. 12 is a flowchart of a method 1200 for interrogating a resonator network as described herein to detect an analyte. For purposes of illustrations, the resonator network of method 1200 includes: (i) a first input resonator that has a dark state and that can enter the dark state in response to receiving illumination at a first input excitation wavelength; (ii) a readout resonator that can receive energy from illumination at a readout wavelength; (iii) a mediating resonator; (iv) an output resonator; (v) a sensor that includes a receptor that preferentially binds to the analyte; and (vi) a backbone. The first input resonator, the readout resonator, the sensor, and the output resonator are coupled to the backbone. The backbone maintains relative locations of the first input resonator, the readout resonator, the mediating resonator, the sensor, and the output resonator such that energy can be transmitted from the readout resonator to the output resonator via the mediating resonator and further such that a probability of energy being transmitted from the readout resonator to the output resonator, when the first input resonator is in the dark state, is related to whether the receptor is bound to an instance of the analyte.

The method 1200 includes illuminating the resonator network, during a first period of time, with light at the first input wavelength (1210). This could include illuminating the sample with one or more pulses of illumination. The duration and/or number of such pulses of such illumination could be specified to ensure that the first input resonator is likely to have entered the dark state, e.g., the provided light at the first input wavelength could be provided for more than a threshold duration of time.

The method 1200 includes illuminating the resonator network, during the first period of time, with light at the readout wavelength (1220). This could include illuminating the sample with one or more pulses of illumination. Such pulses of illumination could be ultrashort pulses, having pulse widths between attoseconds and nanoseconds. The pulses of illumination could have different spectra and/or include different wavelengths of light. For example, a first pulse of illumination could include light at an excitation wavelength of the input resonator of the label and a second pulse of illumination could include light at an excitation wavelength of an input resonator of a different label. In another example, a first pulse of illumination could include light at an excitation wavelength of the input resonator of the label and a second pulse of illumination could include light at an excitation wavelength of a further input resonator of the label. The light at the readout wavelength could be provided subsequent to providing the light at the first input wavelength.

The method 1200 also includes detecting, during the first period of time, an intensity of light emitted from an output resonator of the resonator network (1230). This could include detecting a timing of emission of such light relative to the timing of one or more pulses of light provided at the readout wavelength. Detecting the intensity of light emitted from the resonator network could include detecting a timing of emission of a plurality of photons from a population of resonator networks, e.g., detecting the timing of reception of individual photons using a single photon avalanche diode, a photomultiplier tube, or some other detector element(s). Additionally or alternatively, detecting the timing of emission of a plurality of photons from the sample could include detecting a timing of a peak or other feature of the variation over time of the intensity, rate, or other property of the photons emitted from the sample. Detecting the intensity of light emitted from the resonator network could include detecting a total amount of light emitted from the output resonator, e.g., by integrating a signal related to the intensity of the detected light.

The method 1200 could include additional or alternative steps as described elsewhere herein. The method 1200 could include determining, based on the detected intensity of the emitted light, a presence, amount, count, or other property of the analyte. In some examples, the resonator network could be configured to permit the detection of multiple analytes, e.g., by a process of optically multiplexing and/or addressing multiple different sensors of the resonator network. For example, the resonator network could include a second sensor sensitive to a second analyte and a second input resonator coupled together with the remainder of the resonator network such that a probability of energy being transmitted from the readout resonator to the output resonator, when the second input resonator is in the dark state and the first input resonator is not in the dark state, is related to whether the second receptor is bound to an instance of the second analyte. In such an example, the method 1200 could include, during a second period of time, illuminating the resonator network with light at an excitation wavelength of the second input resonator; illuminating the resonator network with light at the readout wavelength; and detecting an intensity of light emitted from the resonator network during the second period of time. The intensity detected during the second period of time could then be used to determine a concentration, a presence, a count, or some other information about the second analyte. The example method 1200 illustrated in FIG. 12 is meant as an illustrative, non-limiting example. Additional or alternative elements of the method are anticipated, as will be obvious to one skilled in the art.

Figure 13:
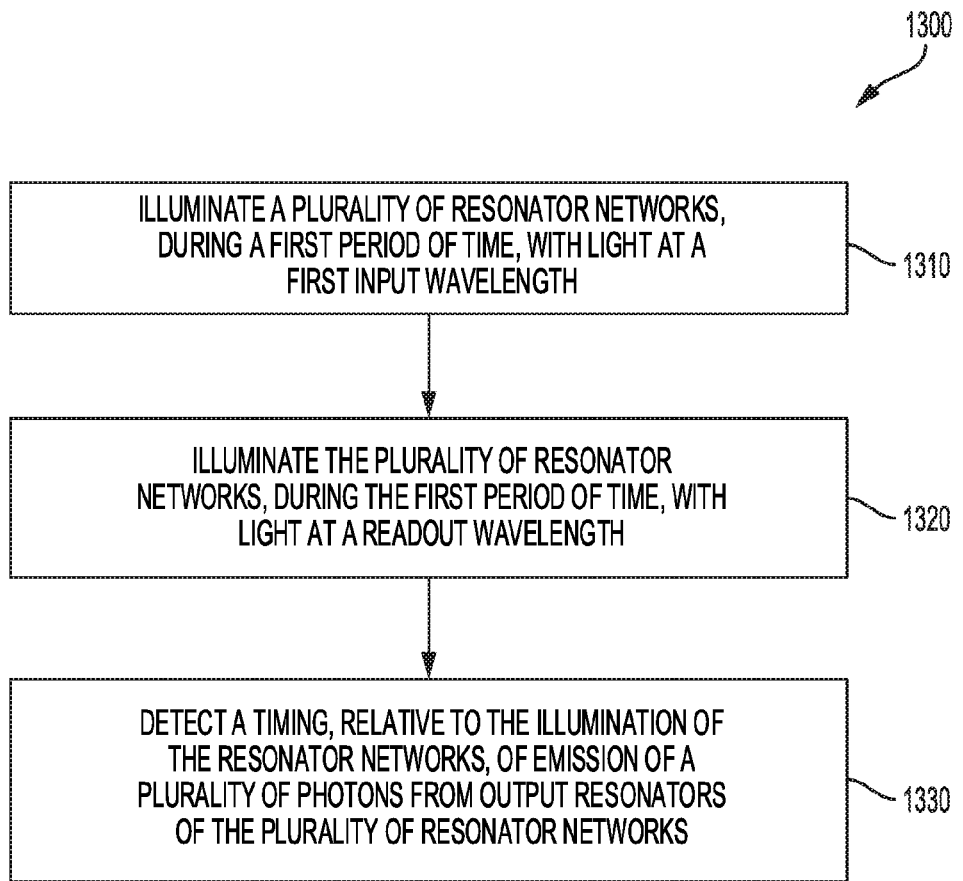
FIG. 13 shows a flow chart of an example method.

FIG. 13 is a flowchart of a method 1300 for using a plurality of resonator networks, as described herein, to generate samples of a random variable. For purposes of illustration, the resonator network identified in method 1300 includes: (i) a first input resonator that has a dark state and that can enter the dark state in response to receiving illumination at a first input wavelength; (ii) a readout resonator that can receive energy from illumination at a readout wavelength; (iii) two or more mediating resonators; (iv) an output resonator; and (v) a backbone. The first input resonator, the readout resonator, the two or more mediating resonators, and the output resonator are coupled to the backbone. The backbone maintains relative locations of the first input resonator, the readout resonator, the two or more mediating resonators, and the output resonator such that energy can be transmitted from the readout resonator to the output resonator via the mediating resonator and further such that the resonator network emits photons from the output resonator, in response to the readout resonator receiving illumination at the readout wavelength, according to a time-dependent probability density function, and wherein a detectable property of the time-dependent probability density function is related to whether the first input resonator is in the dark state.

The method 1300 includes illuminating the plurality of resonator networks, during a first period of time, with light at the first input wavelength (1310). This could include illuminating the sample with one or more pulses of illumination. The duration and/or number of such pulses of such illumination could be specified to ensure that the first input resonator of each of the resonator networks and/or of a specified portion of the resonator networks is likely to have entered the dark state, e.g., the provided light at the first input wavelength could be provided for more than a threshold duration of time.

The method 1300 includes illuminating the plurality of resonator networks, during the first period of time, with light at the readout wavelength (1320). This could include illuminating the sample with one or more pulses of illumination. Such pulses of illumination could be ultrashort pulses, having pulse widths between attoseconds and microseconds.

The method 1300 also includes detecting a timing, relative to the illumination of the resonator networks, of emission of a plurality of photons from the output resonators of the plurality of resonator networks (1330). Detecting the timing of emission of a plurality of photons from the resonator networks could include detecting the timing of reception of individual photons, e.g., using a single photon avalanche diode, a photomultiplier tube, or some other detector element(s). Additionally or alternatively, detecting the timing of emission of a plurality of photons from the sample could include detecting a timing of a peak or other feature of the variation over time of the intensity, rate, or other property of the photons emitted from the sample.

The method 1300 could include additional or alternative steps as described elsewhere herein. For example, the method 1300 could include generating a sample of a random variable based on the detected timing, e.g., by applying a function to the detected timing. The method 1300 could include generating additional samples of the random variable by illuminating the resonator network and detecting a timing of emission of photon(s) responsively emitted from the resonator network. The resonator network could include one or more additional input resonators, and the method 1300 could include, during additional periods of time, generating samples of additional random variables by optically controlling the input resonators of the resonator network such that the resonator network exhibited time-dependent probability density functions corresponding to the additional random variables. The samples of the random variables could be generated by detecting a timing of emission of light from the resonator network in response to illumination. The example method 1300 illustrated in FIG. 13 is meant as an illustrative, non-limiting example. Additional or alternative elements of the method are anticipated, as will be obvious to one skilled in the art.

VIII. Conclusion

"Fluorescent taggants with temporally coded signatures" (Wang, S., Vyas, R., Dwyer, C, "Fluorescent taggants with temporally coded signatures," Optics Express, Vol. 24, No. 14, 11 Jul. 2016) is incorporated herein by reference. All references cited herein are incorporated by reference. In addition, the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A label comprising:
   an input resonator;
   one or more mediating resonators, wherein a first one of the one or more mediating resonators is disposed proximate to the input resonator such that the first mediating resonator can receive energy from the input resonator;
   an output resonator, wherein at least one of the one or more mediating resonators is disposed within the label proximate to the output resonator such that the output resonator can receive energy from the at least one of the one or more mediating resonators;
   a receptor, wherein the receptor is an antibody, aptamer, or protein; and
   a backbone,
   wherein the receptor selectively interacts with an analyte of interest to permit detection of the presence, amount, or location of the analyte of interest in a sample, wherein the input resonator, the output resonator, the one or more mediating resonators, and the receptor are coupled to the backbone, and wherein the backbone maintains relative locations of the input resonator, the output resonator, and the one or more mediating resonators such that energy can be transmitted from the input resonator to the output resonator via the one or more mediating resonators when the receptor is bound to an analyte.

2. The label of claim 1, wherein the backbone comprises two strands of DNA that are at least partially complementary.

3. The label of claim 1, wherein at least one of the mediating resonators, the input resonator, or the output resonator comprises a fluorophore.

4. The label of claim 1, wherein the one or more mediating resonators are disposed within the label as a resonator wire between the input resonator and the output resonator.

5. The label of claim 1, wherein when more than one mediating resonator is present, all of the mediating resonators comprise the same fluorophore.

6. The label of claim 1, wherein the input resonator is a first input resonator, wherein the label further comprises a second input resonator, and wherein at least one of the one or more mediating resonators is disposed proximate to the second input resonator such that the at least one of the one or more mediating resonators can receive energy from the second input resonator.

7. The label of claim 6, wherein the first input resonator is characterized by a first excitation wavelength, and wherein the second input resonator is characterized by a second excitation wavelength that differs from the first excitation wavelength.

8. The label of claim 1, wherein the output resonator is a first output resonator, wherein the label further comprises a second output resonator, wherein at least one of the one or more mediating resonators is disposed within the label proximate to the second output resonator such that the second output resonator can receive energy from the at least one of the one or more mediating resonators.

9. The label of claim 8, wherein the second output resonator is characterized by a second emission wavelength that differs from the emission wavelength of the first output resonator.

10. The label of claim 1, wherein the input resonator absorbs light at an excitation wavelength, wherein the output resonator emits light at an emission wavelength, and wherein the emission wavelength differs from the excitation wavelength.

11. The label of claim 10, wherein the one or more mediating resonators are characterized by respective emission wavelengths, and wherein the emission wavelengths of the one or more mediating resonators are intermediate between the excitation wavelength of the input resonator and the emission wavelength of the output resonator.

12. The label of claim 1, further comprising a facilitator resonator that is coupled to the backbone, wherein the backbone maintains relative locations of the input resonator, the output resonator, the one or more mediating resonators, and the facilitator resonator such that the facilitator resonator being in a dark state facilitates transmission of energy from the input resonator to the output resonator via the one or more mediating resonators.

13. The label of claim 1, further comprising an inhibitor resonator that is coupled to the backbone, wherein the backbone maintains relative locations of the input resonator, the output resonator, the one or more mediating resonators, and the inhibitor resonator such that the inhibitor resonator being in a dark state inhibits transmission of energy from the input resonator to the output resonator via the one or more mediating resonators.

* * * * *